(12) United States Patent
Holsten et al.

(10) Patent No.: US 7,726,539 B2
(45) Date of Patent: Jun. 1, 2010

(54) SURGICAL STAPLING INSTRUMENTS INCLUDING A CARTRIDGE HAVING MULTIPLE STAPLE SIZES

(75) Inventors: Henry E. Holsten, Southington, CT (US); Frank J. Viola, Sandy Hook, CT (US); Clifford L. Emmons, Oakville, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 26 days.

(21) Appl. No.: 12/390,693

(22) Filed: Feb. 23, 2009

(65) Prior Publication Data

US 2009/0152324 A1 Jun. 18, 2009

Related U.S. Application Data

(60) Division of application No. 11/512,943, filed on Aug. 29, 2006, which is a continuation of application No. 11/204,060, filed on Aug. 15, 2005, now Pat. No. 7,407,075.

(51) Int. Cl.
*A61B 17/068* (2006.01)
*A61B 17/072* (2006.01)

(52) U.S. Cl. ............. 227/179.1; 227/176.1; 227/180.1; 227/19

(58) Field of Classification Search ... 227/175.1–182.1, 227/19
See application file for complete search history.

(56) References Cited

U.S. PATENT DOCUMENTS

| | | | |
|---|---|---|---|
| 3,499,591 A | 3/1970 | Green | |
| 4,319,576 A | 3/1982 | Rothfuss | |
| 4,429,695 A | 2/1984 | Green | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,767,044 A | 8/1988 | Green | |
| 4,809,695 A | 3/1989 | Gwathmey et al. | |
| 4,848,637 A | 7/1989 | Pruitt | |
| 4,930,503 A | 6/1990 | Pruitt | |
| 4,941,623 A | 7/1990 | Pruitt | |
| 4,978,049 A | 12/1990 | Green | |
| 5,027,834 A | 7/1991 | Pruitt | |
| 5,180,092 A | 1/1993 | Crainich | |

(Continued)

FOREIGN PATENT DOCUMENTS

EP 0878169 11/1998

(Continued)

OTHER PUBLICATIONS

European Search Report for EP 06016963.8-2318 date of completion is Mar. 9, 2007 (9 pages).

*Primary Examiner*—Rinaldi I. Rada
*Assistant Examiner*—Lindsay Low

(57) ABSTRACT

A surgical stapling apparatus includes a staple cartridge and an anvil member. The staple cartridge includes a plurality of surgical fasteners disposed in rows of retention slots. The staple cartridge may have an annular or linear configuration of retention slots. The tissue contacting surface of the staple cartridge may be tapered or stepped. The anvil member has a tissue contacting surface that includes a number of pockets arranged for substantially aligning with the retention slots. In addition, the tissue contacting surface of the anvil member may complement the tissue contacting surface of the staple cartridge.

14 Claims, 16 Drawing Sheets

U.S. PATENT DOCUMENTS

| | | | |
|---|---|---|---|
| 5,240,163 | A | 8/1993 | Stein et al. |
| 5,342,396 | A | 8/1994 | Cook |
| 5,452,836 | A | 9/1995 | Huitema et al. |
| 5,452,837 | A | 9/1995 | Williamson, IV et al. |
| 5,480,089 | A | 1/1996 | Blewett |
| 5,484,095 | A | 1/1996 | Green et al. |
| 5,497,931 | A | 3/1996 | Nakamura |
| 5,571,116 | A | 11/1996 | Bolanos et al. |
| 5,571,285 | A | 11/1996 | Chow et al. |
| 5,676,674 | A | 10/1997 | Bolanos et al. |
| 5,697,542 | A | 12/1997 | Knodel et al. |
| 5,709,680 | A | 1/1998 | Yates et al. |
| 5,865,361 | A | 2/1999 | Milliman et al. |
| 5,871,135 | A | 2/1999 | Williamson, IV et al. |
| 5,915,616 | A | 6/1999 | Viola et al. |
| 5,964,394 | A | 10/1999 | Robertson |
| 6,202,914 | B1 | 3/2001 | Geiste et al. |
| 6,325,810 | B1 | 12/2001 | Hamilton et al. |
| 6,669,073 | B2 | 12/2003 | Milliman et al. |
| 6,786,382 | B1 | 9/2004 | Hoffman |
| 6,905,057 | B2 | 6/2005 | Swayze et al. |
| 6,959,852 | B2 | 11/2005 | Shelton, IV et al. |
| 6,964,363 | B2 | 11/2005 | Wales et al. |
| 6,978,921 | B2 | 12/2005 | Shelton, IV et al. |
| 6,988,649 | B2 | 1/2006 | Shelton, IV et al. |
| 7,000,818 | B2 | 2/2006 | Shelton, IV et al. |
| 7,000,819 | B2 | 2/2006 | Swayze et al. |
| 7,044,352 | B2 | 5/2006 | Shelton, IV et al. |
| 7,055,731 | B2 | 6/2006 | Shelton, IV et al. |
| 7,059,508 | B2 | 6/2006 | Shelton, IV et al. |
| 7,070,083 | B2 | 7/2006 | Jankowski |
| 7,114,642 | B2 | 10/2006 | Whitman |
| 2004/0004105 | A1 | 1/2004 | Jankowski |
| 2004/0232195 | A1 | 11/2004 | Shelton et al. |
| 2004/0232199 | A1 | 11/2004 | Shelton et al. |
| 2005/0006430 | A1 | 1/2005 | Wales |
| 2005/0006431 | A1 | 1/2005 | Shelton et al. |
| 2005/0006434 | A1 | 1/2005 | Wales et al. |
| 2005/0023324 | A1 | 2/2005 | Doll et al. |
| 2005/0070925 | A1 | 3/2005 | Shelton et al. |
| 2005/0070958 | A1 | 3/2005 | Swayze et al. |
| 2005/0173490 | A1 | 8/2005 | Shelton, IV |
| 2005/0178813 | A1 | 8/2005 | Swayze et al. |
| 2005/0187576 | A1 | 8/2005 | Whitman et al. |
| 2005/0263562 | A1 | 12/2005 | Shelton et al. |
| 2006/0000868 | A1 | 1/2006 | Shelton et al. |
| 2006/0022014 | A1 | 2/2006 | Shelton et al. |
| 2006/0022015 | A1 | 2/2006 | Shelton et al. |
| 2006/0025809 | A1 | 2/2006 | Shelton, IV |
| 2006/0025810 | A1 | 2/2006 | Shelton, IV |
| 2006/0025811 | A1 | 2/2006 | Shelton, IV |
| 2006/0025812 | A1 | 2/2006 | Shelton, IV |
| 2006/0025813 | A1 | 2/2006 | Shelton et al. |
| 2006/0025816 | A1 | 2/2006 | Shelton, IV |
| 2006/0025817 | A1 | 2/2006 | Ortiz et al. |
| 2006/0049230 | A1 | 3/2006 | Shelton et al. |
| 2006/0097026 | A1 | 5/2006 | Shelton, IV |
| 2006/0226196 | A1 | 10/2006 | Hueil et al. |
| 2007/0010838 | A1 | 1/2007 | Shelton et al. |
| 2007/0045379 | A1 | 3/2007 | Shelton |

FOREIGN PATENT DOCUMENTS

| | | |
|---|---|---|
| EP | 0878169 A1 | 11/1998 |
| EP | 1090592 | 4/2001 |
| EP | 1090592 A1 | 4/2001 |
| EP | 1316290 | 11/2002 |
| EP | 1316290 A2 | 6/2003 |
| EP | 1479346 | 5/2004 |
| EP | 1479346 A1 | 11/2004 |
| EP | 1728473 | 12/2006 |
| FR | 2 838 952 A | 10/2003 |
| FR | 2838952 | 10/2003 |
| SU | 405234 | 9/1975 |
| SU | 1333319 | 8/1987 |
| SU | 1442191 | 12/1988 |
| SU | 1459659 | 2/1989 |
| SU | 1442191 | 12/1998 |
| WO | WO 90/05489 | 5/1990 |
| WO | WO 90/05489 A | 5/1990 |
| WO | WO 97/34533 | 9/1997 |
| WO | WO 97/34533 A | 9/1997 |
| WO | WO 03/094743 | 11/2003 |
| WO | WO 03/094743 A | 11/2003 |
| WO | WO 03/094747 | 11/2003 |
| WO | WO 03/094747 A1 | 11/2003 |

SURGICAL STAPLING INSTRUMENTS INCLUDING A CARTRIDGE HAVING MULTIPLE STAPLE SIZES

CROSS-REFERENCE TO RELATED APPLICATIONS

This application is a division of U.S. patent application Ser. No. 11/512,943, filed Aug. 29, 2006, which is a continuation of U.S. patent application Ser. No. 11/204,060, filed Aug. 15, 2005, now U.S. Pat. No. 7,407,075. The entire contents of each of these prior applications are hereby incorporated by reference herein.

BACKGROUND

1. Technical Field

The present disclosure relates to surgical stapling instruments and, more particularly, to surgical stapling instruments including a cartridge having multiple staple sizes.

2. Background of Related Art

There are several known types of surgical stapling instruments specifically adapted for use in various procedures such as end-to-end anastomosis, gastrointestinal anastomosis, endoscopic gastrointestinal anastomosis, and transverse anastomosis. Examples of stapling instruments for these various procedures can be found in U.S. Pat. Nos. 5,915,616; 6,202,914; 5,865,361; and 5,964,394.

Each surgical stapling instrument includes an anvil which is approximated relative to a staple cartridge. The staple cartridge typically has one or more laterally spaced rows of staples which, depending on the particular stapling instrument, may be arranged in a linear or non-linear configuration. The anvil includes staple forming depressions which are aligned with and/or in registration with the staple slots of the staples in the cartridge. In use, each of the surgical stapling instruments involves the gripping of tissue to be fastened, the ejecting of individual staples, the forcing of staples through the gripped tissue and the closing and/or forming of the staples against the staple forming depressions of the anvil.

A common issue in transecting tissue and/or in anastomosis procedures, employing any one of the surgical stapling instruments disclosed above, is the balance between anastomotic strength and the degree of hemostasis achievable. It is known to include different size staples in a surgical stapling apparatus having a constant gap (i.e. a uniform distance) between an anvil and a staple cartridge.

SUMMARY

The present disclosure is directed towards surgical stapling instruments configured to effectuate an improved balance between the anastomotic strength and the degree of hemostasis at the tissue interface. In particular, embodiments of the present disclosure include surgical fasteners of different sizes. Further still, the distance between an anvil member and a staple cartridge (i.e. the gap) varies from a centerline of the staple cartridge to an outer edge of the staple cartridge. Combining the different sizes of surgical fasteners with the varying gap between the anvil member and the staple cartridge improves the anastomotic strength and the degree of hemostasis at the tissue interface.

According to one aspect of the disclosure, the surgical stapling instrument includes a first structure defining having an anvil member operatively associated therewith, and a second structure defining a staple cartridge operatively associated therewith. The staple cartridge has a tissue contacting surface with a stepped cross-sectional profile. The tissue contacting surface of the staple cartridge also includes a plurality of retention slots formed therein for retaining a surgical fastener. During operation of the surgical stapling instrument, the anvil member and the staple cartridge can be approximated relative to one another.

The stepped tissue contact surface of the staple cartridge defines a plurality of tissue contacting surfaces each having a different height. In one embodiment, the stepped tissue contacting surface of the cartridge includes an inner tissue contacting surface having a height, an intermediate tissue contacting surface having a height less than the height of the inner tissue contacting surface, and an outer tissue contacting surface having a height less than the height of the intermediate tissue contacting surface.

The inner, intermediate, and outer tissue contacting surfaces each include at least one row of retention slots formed therein. A plurality of surgical fasteners is disposed, one each, in each retention slot. Each surgical fastener includes a backspan and a pair of descending legs.

The surgical fasteners retained in the retention slots formed in the inner tissue contacting surface have a first leg length, the surgical fasteners retained in the retention slots formed in the intermediate tissue contacting surface have a second leg length, and the surgical fasteners retained in the retention slots formed in the outer tissue contacting surface have a third leg length. In one embodiment, the surgical fasteners retained in the retention slots formed in the inner tissue contacting surface have a leg length of about 2.3 mm, while the surgical fasteners retained in the retention slots formed in the intermediate tissue contacting surface have a leg length of about 3.5 mm, and the surgical fasteners retained in the retention slots formed in the outer tissue contacting surface have a leg length of about 4.1 mm.

It is envisioned that the surgical stapling instrument can be a circular-type surgical stapling instrument wherein the anvil member and the staple cartridge can be annular. In one embodiment, the plurality of tissue contacting surfaces decreases in height in a radially outward direction. Accordingly, the inner tissue contacting surface is closest to the center and the outer tissue contacting surface is furthest from the center of the annular staple cartridge. Moreover, surgical fasteners having relatively short leg lengths are retained in the retention slots closest to the center of the annular staple cartridge while surgical fasteners having relatively longer leg lengths are retained in the retention slots furthest from the center of the annular staple cartridge.

It is further envisioned that the surgical stapling instrument can be a linear-type surgical stapling instrument wherein the anvil member and the staple cartridge are linear. In these instruments, the staple cartridge and/or the anvil member may define a knife cut line. Accordingly, the plurality of tissue contacting surfaces decreases in height in a direction orthogonally outward from the knife cut line. In particular, the inner tissue contacting surface is closest to the knife cut line while the outer tissue contacting surface is furthest from the knife cut line. In addition, surgical fasteners having relatively short leg lengths are retained in the retention slots closest to the knife cut line while surgical fasteners having relatively longer leg lengths are retained in the retention slots furthest from the knife cut line.

It is envisioned that the anvil member can have a tissue contacting surface with a stepped cross-sectional profile including a plurality of tissue contacting surfaces, wherein each tissue contacting surface has a different height. In addition, each one of the plurality of tissue contacting surfaces can include at least one annular and/or linear row of surgical fastener forming depressions formed therein.

In one embodiment, the anvil member can have a tissue contacting surface which is shaped (i.e. stepped) to complement the stepped tissue contacting surface of the staple cartridge. In another embodiment, the anvil member can have a tissue contacting surface which is stepped while the tissue contacting surface of the staple cartridge is substantially planar. In yet another embodiment, the anvil member can have a tissue contacting surface which is shaped to substantially complement the stepped tissue contacting surface of the staple cartridge (i.e. the depths of the tissue contacting surfaces of the stepped anvil member are not equal to the heights of the individual tissue contacting surfaces of the tissue contacting surface of the staple cartridge). In still another embodiment, the anvil member can have a tissue contacting surface which is stepped to mirror the tissue contacting surface of the staple cartridge (i.e. the depths of individual tissue contacting surfaces of the tissue contacting surface of the anvil member are substantially equal to the depths of the individual tissue contacting surfaces of the staple cartridge).

In other embodiments of the present disclosure, a surgical stapling instrument includes an operative tool disposed at one end thereof. The operative tool includes an anvil member and a staple cartridge. The staple cartridge may be included in a disposable surgical stapling apparatus or in a reusable surgical stapling apparatus. Further still, a replaceable loading unit may be located in either the disposable or the reusable surgical stapling apparatus. In one embodiment, the replaceable loading unit includes a staple cartridge, while an alternate embodiment of the replaceable loading unit includes a staple cartridge and an anvil member. In particular, the staple cartridge includes a plurality of surgical fasteners disposed in rows of retention slots. The surgical fasteners may have different leg lengths wherein a plurality of surgical fasteners having substantially the same leg length is disposed in a row. A number of fastener ejection members are disposed in the staple cartridge wherein each fastener ejection member includes a plurality of staple pushers for ejecting the surgical fasteners in cooperation with an actuation mechanism.

The staple cartridge may include an angled tissue contacting surface that peaks at a centerline of the staple cartridge and tapers towards outer walls of the staple cartridge. Alternatively, the tissue contacting surface of the staple cartridge may have a surface that is parallel with the bottom surface of the staple cartridge or parallel to a plane defined by the backspans of surgical fasteners disposed in a selected row. The parallel surface of the tissue contacting surface has a width dimension that is sufficient to accommodate at least one row of surgical fasteners. The staple cartridge may include a knife channel.

In cooperation with the presently disclosed staple cartridge, the anvil member may include a planar tissue contacting surface that is substantially parallel to the bottom surface of the staple cartridge or parallel to a plane defined by the backspans of surgical fasteners disposed in a selected row. In the alternative, the tissue contacting surface of the anvil member may be angled in an opposed manner to the angle of the tissue contacting surface of the staple cartridge. Further still, the tissue contacting surface of the anvil member may have a planar surface that is substantially parallel to the bottom surface of the staple cartridge or parallel to a plane defined by the backspans of surgical fasteners disposed in a selected row and tapered surfaces that define angles opposite to the angles defined by the tissue contacting surface of the staple cartridge. The parallel surfaces of the anvil member have a width dimension that corresponds to a width dimension of the parallel surface of the staple cartridge.

It is further contemplated that one embodiment of the surgical stapling apparatus includes structures for supplemental sealing of the fastened layers of tissue. In one embodiment, the surgical stapling apparatus includes a wound closure assembly having a reservoir and a supply line. The reservoir is adapted for storing a quantity of a wound closure material and is fluidly coupled to the staple cartridge via the supply line for delivering amounts of the wound closure material to the plurality of retention slots.

The presently disclosed surgical stapling instruments, together with attendant advantages, will be more clearly illustrated below by the description of the drawings and the detailed description of the embodiments.

Other objects and features of the present disclosure will become apparent from consideration of the following description taken in conjunction with the accompanying drawings.

BRIEF DESCRIPTION OF THE DRAWINGS

Embodiments of the presently disclosed surgical stapling apparatus are described herein with reference to the accompanying drawings, wherein.

DETAILED DESCRIPTION OF EMBODIMENTS

Figure 1:
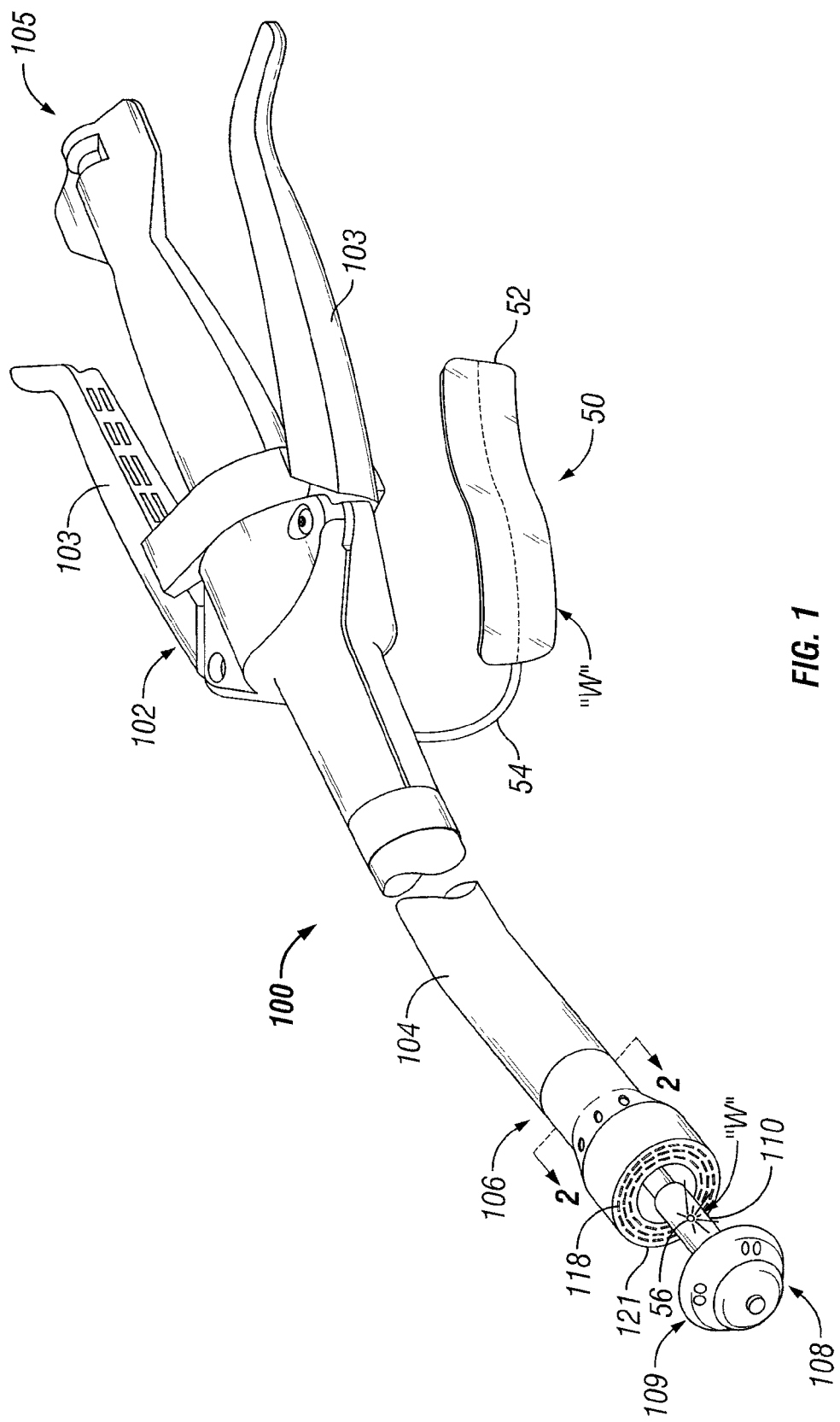
FIG. 1 is a perspective view of a surgical stapling instrument constructed in accordance with the present disclosure.

Embodiments of the presently disclosed surgical stapling instruments will now be described in detail with reference to the drawing figures wherein like reference numerals identify similar or identical elements. In the drawings and in the description which follows, the term "proximal", as is traditional, will refer to the end of the surgical stapling instrument which is closest to the operator while the term "distal" will refer to the end of the device which is furthest from the operator.

The present disclosure relates to a staple cartridge and an anvil member for use in a disposable or re-usable surgical stapling apparatus. The presently disclosed staple cartridge and anvil member, as will be discussed in detail hereinbelow, may be used with any of the surgical stapling apparatus shown in FIG. 1, 4, 5, or 6. In addition, a replaceable loading unit may be located in either the disposable or the reusable surgical stapling apparatus. In one embodiment, the replaceable loading unit includes a staple cartridge, including any of the staple cartridges disclosed herein. Alternatively, the replaceable loading unit includes the staple cartridge and an anvil member, including any of the anvil members disclosed herein. In combination with the disposable or the reusable surgical stapling apparatus, the replaceable loading unit provides improved flexibility of the respective surgical stapling apparatus in that the respective surgical stapling apparatus is readily adaptable for different stapling procedures.

Figure 2:
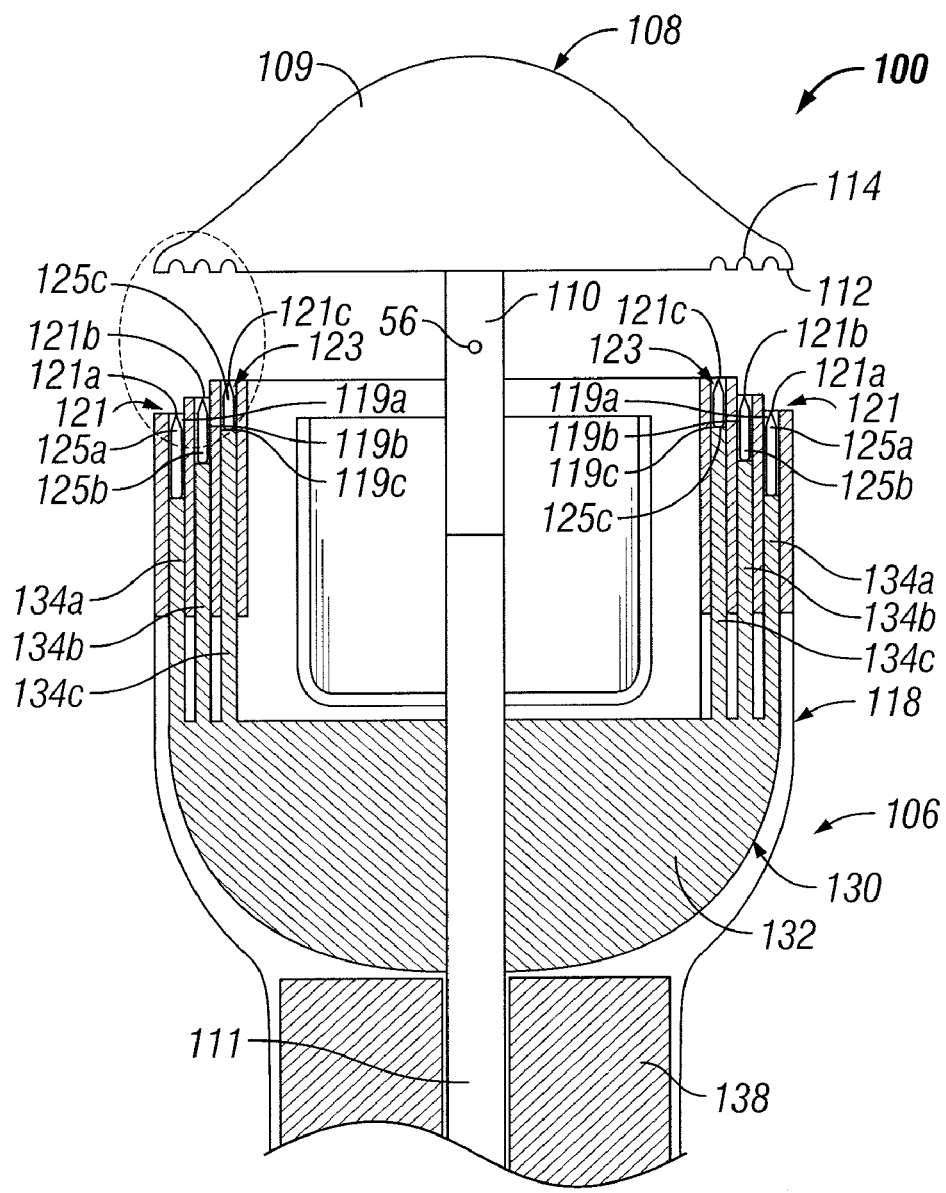
FIG. 2 is a schematic cross-sectional side elevational view of the distal end portion of the surgical stapling instrument of FIG. 1, as taken through 2-2 of FIG. 1.

Referring now in detail to FIGS. 1-2, in which like reference numerals identify similar or identical elements, a surgical stapling instrument, in accordance with a first embodiment of the disclosure, is generally designated as 100.

As seen in FIG. 1, surgical stapling instrument 100 includes a handle assembly 102 having at least one pivotable actuating handle member 103, and further includes advancing means 105. Extending from handle assembly 102, there is provided a tubular body portion 104 which may be constructed so as to have a curved shape along its length. Tubular body portion 104 terminates in a fastener ejection member assembly 106 having a circular staple cartridge 118 including a tissue contacting surface 121 disposed at a distal end thereof.

As seen in FIG. 2, tissue contacting surface 121 is stepped including an outer tissue contacting surface 121a, an intermediate tissue contacting surface 121b, and an inner tissue contacting surface 121c. Each tissue contacting surface 121a-121c has a different height from one another as measured from a bottom surface 131 of a staple pusher or fastener ejection member 130. Specifically, tissue contacting surfaces 121a-121c are planar structures that are substantially parallel to one another, but are not co-planar (i.e. stepped) with one another. In addition, each tissue contacting surface 121a-c defines a planar axis that extends through the respective tissue contacting surface 121a-c. A first wall surface interconnects tissue contacting surfaces 121a and 121b, while a second wall surface interconnects tissue contacting surfaces 121b and 121c. The first and second wall surfaces are planar structures wherein each wall surface defines a planar axis. In one embodiment, the planar axes of the wall surfaces are orthogonal to the planar axes of tissue contacting surfaces 121a-c.

Inner tissue contacting surface 121c has the greatest height, outer tissue contacting surface 121a has the least height, and intermediate tissue contacting surface 121b has a height between the heights of outer and inner tissue contacting surfaces 121a, 121c. While tissue contacting surfaces 121a-121c are shown as increasing in height from outer tissue contacting surface 121a to inner tissue contacting surface 121c (i.e. radially inward), it is within the scope of the present disclosure that the heights of each tissue contacting surface can vary depending on the particular surgical procedure. For example, tissue contacting surfaces 121a-121c can increase in height in a radially outward direction, the intermediate tissue contacting surface 121b can be the highest or the lowest tissue contacting surface, or at least two of tissue contacting surfaces 121a-121c can have the same height.

In one embodiment, each tissue contacting surface 121a-121c includes a respective annular row 119a-119c of retention slots 123 formed therein. Each retention slot 123 of annular rows 119a-119c is configured and dimensioned to retain a staple or surgical fastener 125 therein. Each surgical fastener 125 includes a backspan (not shown) and a pair of depending legs 25. In one embodiment, each annular row 119a-119c of slots 123 includes a respective surgical fastener 125a-125c having its own characteristic features.

As seen in FIG. 2, legs 25a of surgical fasteners 125a have a first leg length, legs 25b of surgical fasteners 125b have a second leg length, and legs 25c of surgical fasteners 125c have a third leg length. In particular, surgical fasteners 125a-125c increase in height in a radially outward direction. In one embodiment, legs 25c of surgical fasteners 125c have a leg length of about 2.3 mm, legs 25b of surgical fasteners 125b have a leg length of about 3.5 mm, and legs 25a of surgical fasteners 125a have a leg length of about 4.1 mm. As such, inner tissue contacting surface 121c has the greatest height and retains surgical fasteners 125c having the shortest leg lengths, and outer tissue contacting surface 121a has the least height and retains surgical fasteners 125a having the longest leg lengths. Having tissue contacting surface 121 step progressively downward at intermediate tissue contacting surface 121b and then again at outer tissue contacting surface 121a results in the formation of surgical fasteners 125b and 125c, respectively. It is envisioned and within the scope of the present disclosure that any number of arrangements are possible.

While a single annular row 119a-119c of retention slots 123 is shown for each tissue contacting surface 121a-121c, it is envisioned and within the scope of the present disclosure that each tissue contacting surface 121a-121c can include multiple annular rows of retention slots.

As seen in FIG. 2, a fastener ejection assembly 106 of surgical stapling instrument 100 includes fastener ejection member 130 disposed within staple cartridge 118. Fastener ejection member 130 includes a proximal portion 132 having a generally frusto-conical shape and a distal portion defining concentric rings of peripherally spaced staple pushers 134a-c, each one of which is received within a respective staple retention slot 123 and is cooperative with its respective surgical fastener 125a-c disposed in annular rows 119a-c. In one embodiment, it is envisioned that proximal portion 132 of fastener ejection member 130 is configured and dimensioned to be contacted by a distal end of a driver tube 138. Hence, upon advancing fastener ejection member 130 by advancing driver tube 138, staple pushers 134a-c will pass further into retention slots 123 thereby pushing surgical fasteners 125 contained therein axially outward.

In an alternate embodiment, staple pushers 134a-c of fastener ejection member 130 have different heights for cooperating with different sized surgical fasteners. In particular, staple pushers 134a-c are sized such that when surgical fasteners 125a-c are disposed in their respective annular rows 119a-c, tips of surgical fasteners 125a-c are located substantially in the same plane despite the difference in leg lengths between each row of surgical fasteners.

Surgical stapling instrument 100 further includes a circular anvil assembly 108 having an anvil head 109 and an anvil shaft 110 extending from a proximal end thereof and adapted to engage a shaft 111 extending distally from staple cartridge 118. Anvil head 109 includes an annular anvil member 112 disposed at a proximal end thereof, wherein anvil member 112 includes at least one, row of fastener forming depressions 114 formed circumferentially thereabout. In one embodiment, surgical stapling instrument 100 includes three laterally spaced rows of fastener forming depressions 114 formed circumferentially thereabout. Each fastener forming depression 114 is in registration with a corresponding retention slot 123.

Figure 3A:
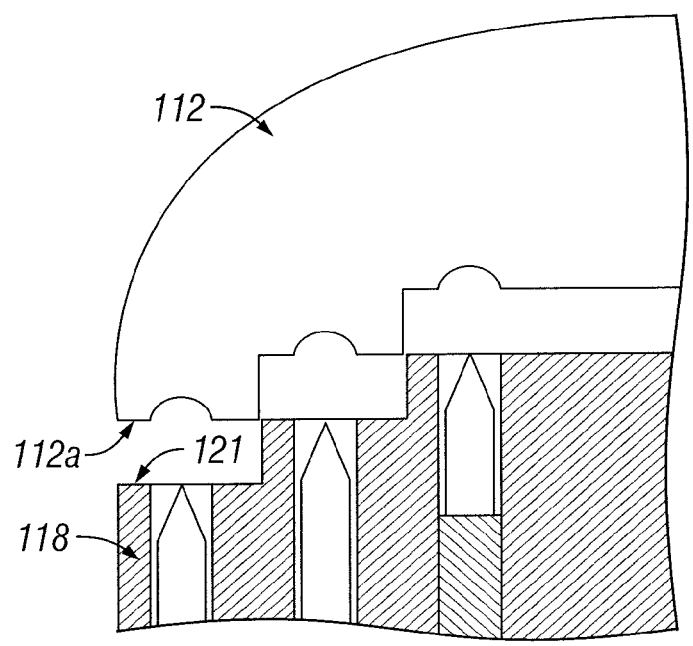
FIG. 3A is an enlarged schematic representation of the indicated area of FIG. 2, illustrating tissue contacting surfaces in accordance with an alternate embodiment of the present disclosure.
Figure 3B:
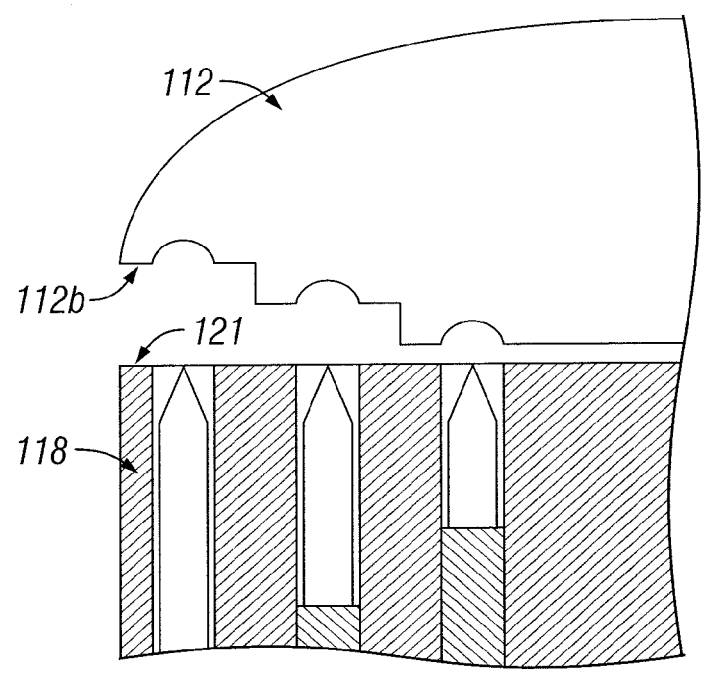
FIG. 3B is an enlarged schematic representation of the indicated area of FIG. 2, illustrating tissue contacting surfaces in accordance with another embodiment of the present disclosure.
Figure 3C:
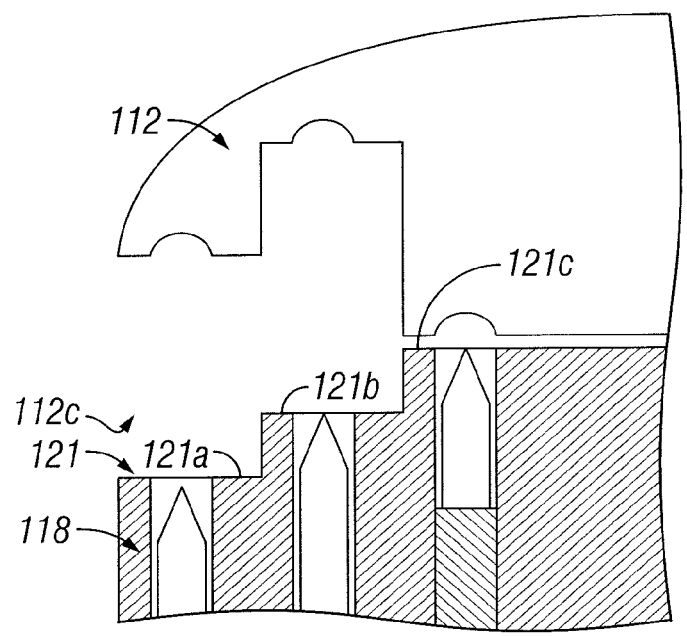
FIG. 3C is an enlarged schematic representation of the indicated area of FIG. 2, illustrating tissue contacting surfaces in accordance with still another embodiment of the present disclosure.
Figure 3D:
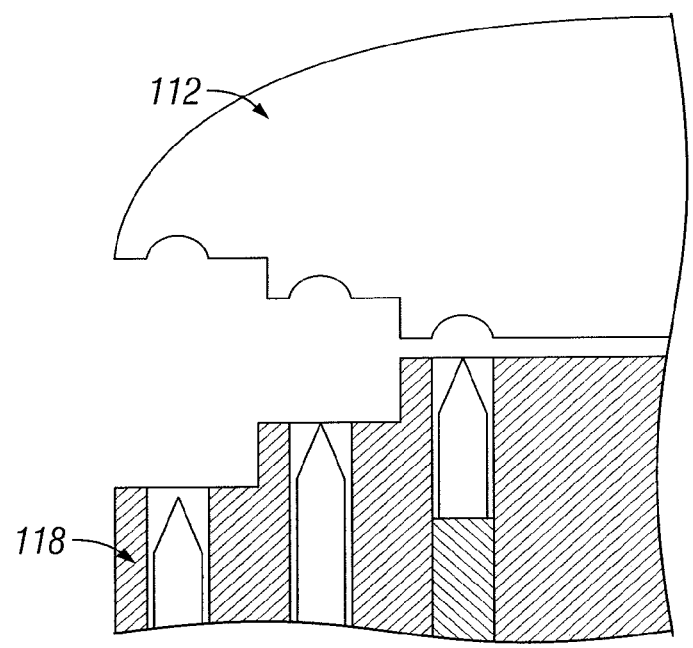
FIG. 3D is an enlarged schematic representation of the indicated area of FIG. 2, illustrating tissue contacting surfaces in accordance with a further embodiment of the present disclosure.

While anvil member 112 is shown in FIG. 2 as having a substantially planar tissue contacting surface, it is envisioned and within the scope of the present disclosure for surgical stapling instrument 100 to have a number of alternate configurations. For example, as seen in FIG. 3A, anvil member 112 can have a tissue contacting surface 112a which is shaped (i.e. stepped) to complement stepped tissue contacting surface 121 of staple cartridge 118 or, as seen in FIG. 3B, anvil member 112 can have a tissue contacting surface 112b which is stepped while tissue contacting surface 121 of staple cartridge 118 is substantially planar. In addition, for example, as seen in FIG. 3C, anvil member 112 can have one row of staple pockets 114b that extends a greater distance than staple pockets 114a or 114c into anvil member 112 for accommodating surgical fasteners having a longer leg length or, as seen in FIG. 3D, anvil member 112 can have a tissue contacting surface 112d which is stepped to mirror tissue contacting surface 121 of staple cartridge 118 (i.e. the depths of individual tissue contacting surfaces of tissue contacting surface 112d of anvil member 112 are substantially equal to the depths of the individual tissue contacting surfaces 121a-121c of staple cartridge 118).

The sizes of surgical fasteners 125a-125c are selected and intended for use in gastric firings typically required in bariatric procedures. However, it is envisioned and within the scope of the present disclosure that the sizes of surgical fasteners 125a-125c selected can be chosen for performance in different types of tissue, such as, for example, the colon, bowels, lungs, the bronchus, pulmonary vessels, the liver, and the like.

In operation, surgical stapling instrument 100 is positioned within a tubular organ in the body of the patient and the ends of the organ to be joined are positioned in a gap between staple cartridge 118 and anvil assembly 108. As is conventional, the ends of the organ may be secured around anvil shaft 110 by a purse string suture prior to approximation of anvil assembly 108 to staple cartridge 118. Surgical stapling instrument 100 is then approximated and fired. An example of a surgical stapling apparatus and methods for its use are disclosed in U.S. Pat. No. 5,915,616, currently assigned to Tyco Healthcare Group LP, the entire contents of which is incorporated herein by reference.

Figure 4:
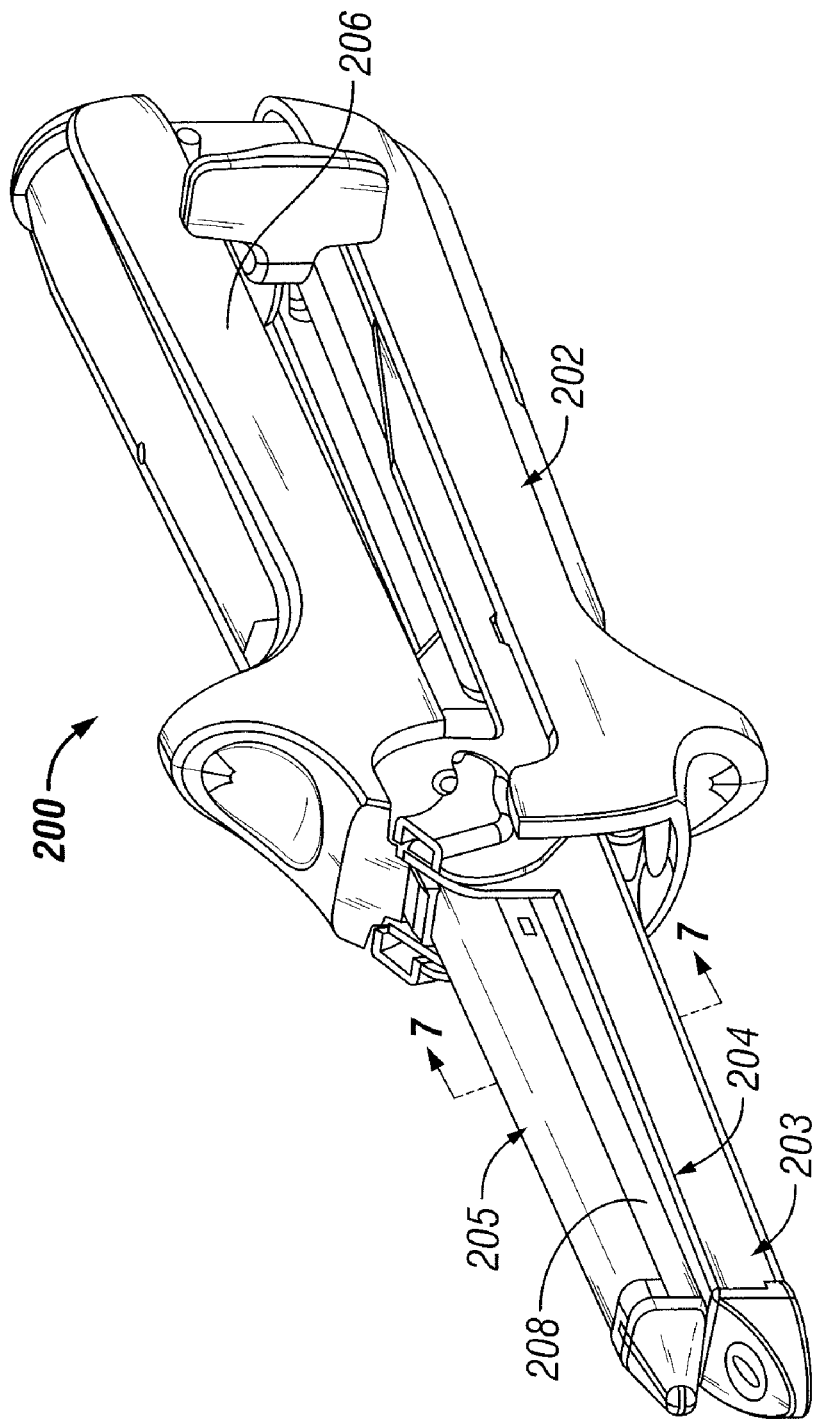
FIG. 4 is a perspective view of an alternative surgical stapling instrument constructed in accordance with the present disclosure.
Figure 7:
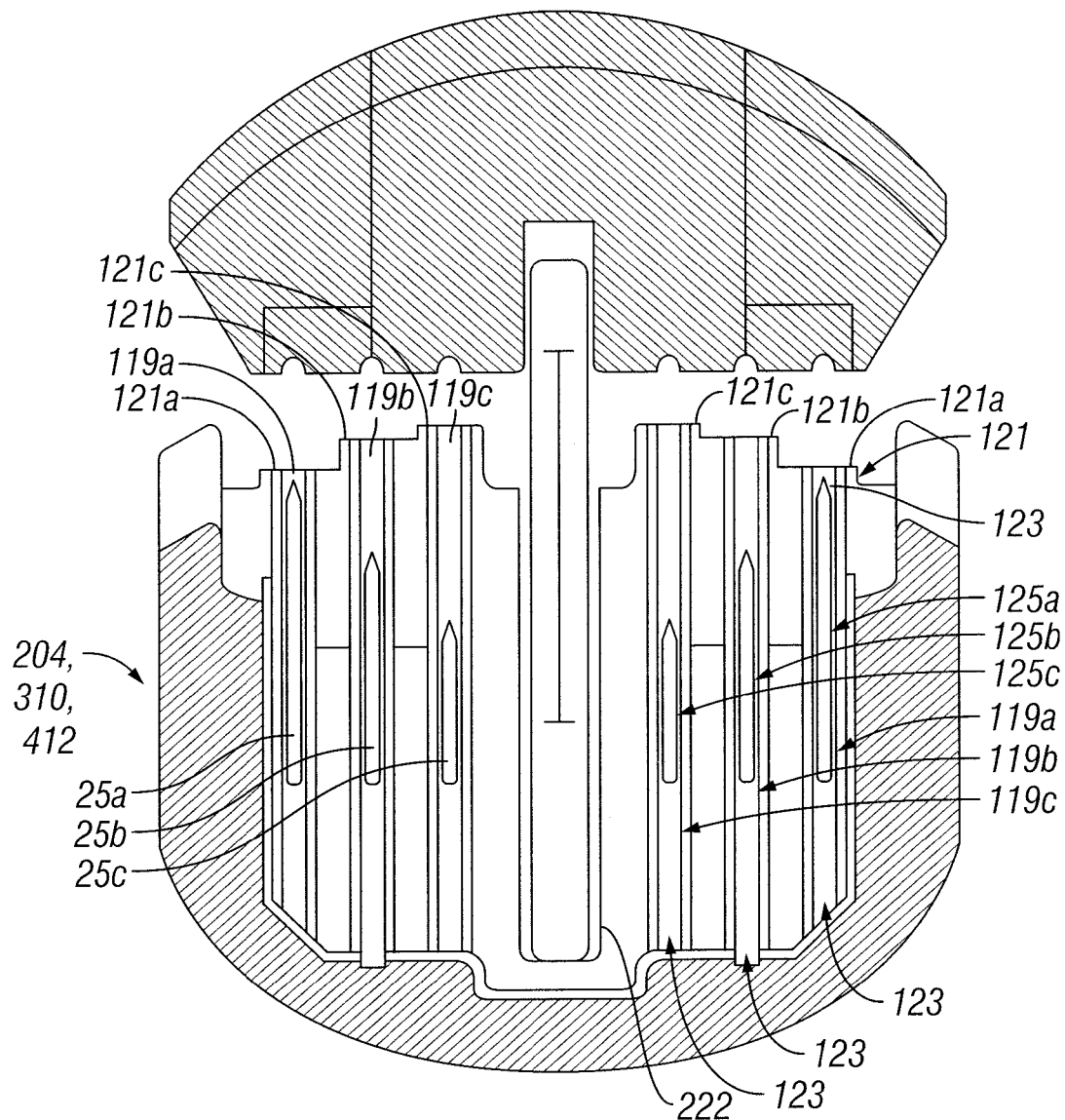
FIG. 7 is a schematic cross-sectional side elevational view of the distal end portion of the surgical stapling instruments of FIGS. 4-6, as taken through 7-7 of each of FIGS. 4-6.

Turning now to FIGS. 4 and 7, a surgical stapling instrument, of the gastro-intestinal anastomosis type for performing surgical anastomotic stapling, in accordance with another embodiment of the disclosure, is generally designated as 200. Surgical stapling instrument 200 includes a first handle 202 having a jaw 230 defining a staple cartridge receiving section extending from a distal end thereof, a staple cartridge 204 receivable in jaw 203, a second handle 206 having a jaw 205 defining an anvil member receiving section extending from a distal end thereof, and an anvil member 208 operatively associated with jaw 205. First and second handles 202, 206 are configured such that staple cartridge 204 is substantially aligned with anvil member 208.

As seen in FIG. 7, staple cartridge 204 includes a stepped tissue contacting surface 121 including an outer tissue contacting surface 121a, an intermediate tissue contacting surface 121b, and an inner tissue contacting surface 121c, each of which has a different height from one another as measured from a bottom surface 231 of staple cartridge 204. Tissue contacting surfaces 121a-121c are planar structures that are substantially parallel to one another, but are not co-planar with one another. For example, tissue contacting surfaces 121a-121c, as shown in FIG. 7, can decrease in height in a direction orthogonally outward from knife track 222. In embodiments that do not include knife track 222, tissue contacting surfaces 121a-c decrease in height in a direction orthogonally outward from a centerline of staple cartridge 204.

Each tissue contacting surface 121a-121c includes a respective linear row 119a-119c of retention slots 123 formed therein. Each retention slot 123 of linear rows 119a-119c is configured and dimensioned to retain a surgical fastener 125 therein. Each linear row 119a-119c of slots 123 includes a respective surgical fastener 125a-125c having its own characteristic features.

As seen in FIG. 7, legs 25a of surgical fasteners 125a have a first leg length of about 4.1 mm, legs 25b of surgical fasteners 125b have a second leg length of about 3.5 mm, and legs 25c of surgical fasteners 125c have a third leg length of about 2.3 mm. In particular, surgical fasteners 125a-125c increase in height in an orthogonally outward direction relative towards optional knife track 222. Knife track 222 is disposed along a centerline of staple cartridge 204, 310, or 412 and is adapted for slidably receiving an optional knife (not shown). Having tissue contacting surface 121 step progressively downward at intermediate tissue contacting surface 121b and then again at outer tissue contacting surface 121a results in the formation of surgical fasteners 125b and 125c, respectively. It is envisioned and within the scope of the present disclosure that any number of arrangements are possible.

In operation, surgical stapling instrument 200 is fired similarly to and in accordance with other known surgical stapling instruments. An example of a surgical stapling apparatus and methods for its use are is disclosed in U.S. Pat. No. 6,202,914, currently assigned to Tyco Healthcare Group LP, the entire contents of which is incorporated herein by reference.

Figure 16:
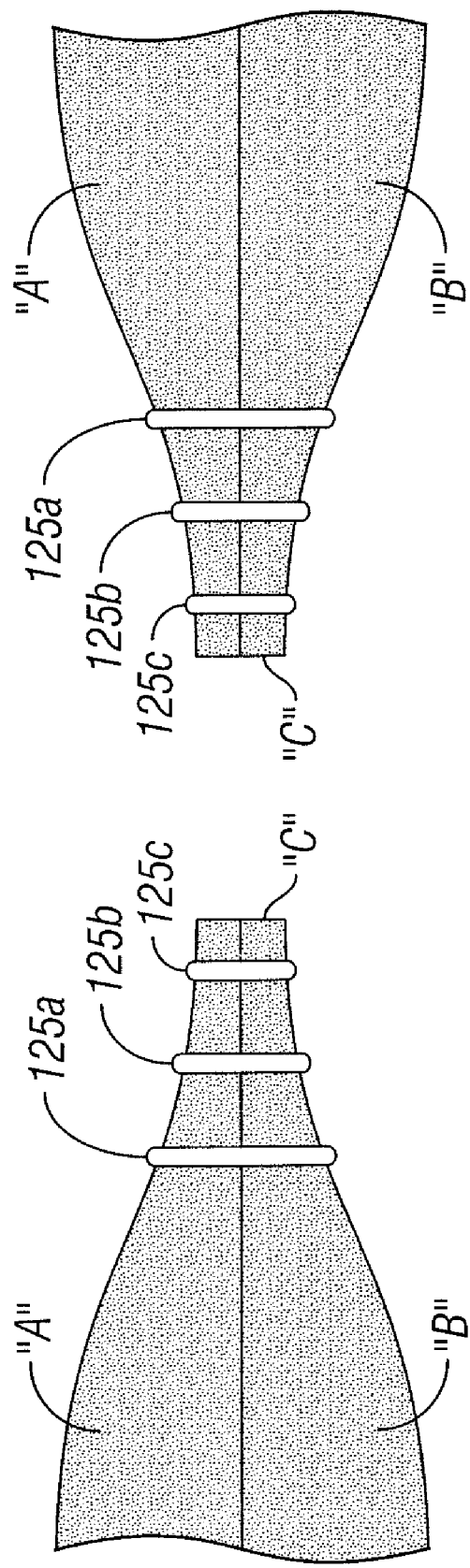
FIG. 16 is a cross-sectional side elevational view of the resulting tissue interface following the firing of surgical stapling instrument of FIGS. 7 and 10-15.

Referring additionally to FIG. 16, following the firing of surgical stapling instrument 200, the resulting tissue interface is seen in cross-section. Accordingly, surgical fasteners 125a and 125b (i.e. the two rows of surgical fasteners furthest from knife cut line "C") serve to hold tissues "A" and "B" to one another while surgical fasteners 125c (i.e. the row of surgical fasteners closest to knife cut line "C") serve to provide the hemostasis.

While surgical stapling instrument 200 is a linear-type surgical stapler, it is envisioned and within the scope of the present disclosure, that surgical stapling instrument 200 can include a tissue contacting surface having a cross-sectional profile for at least one of the anvil member and the staple cartridge which is substantially similar to the tissue contacting surfaces of the anvil member and the staple cartridge of surgical stapling instrument 100, as shown in FIGS. 3A-3D.

Figure 5:
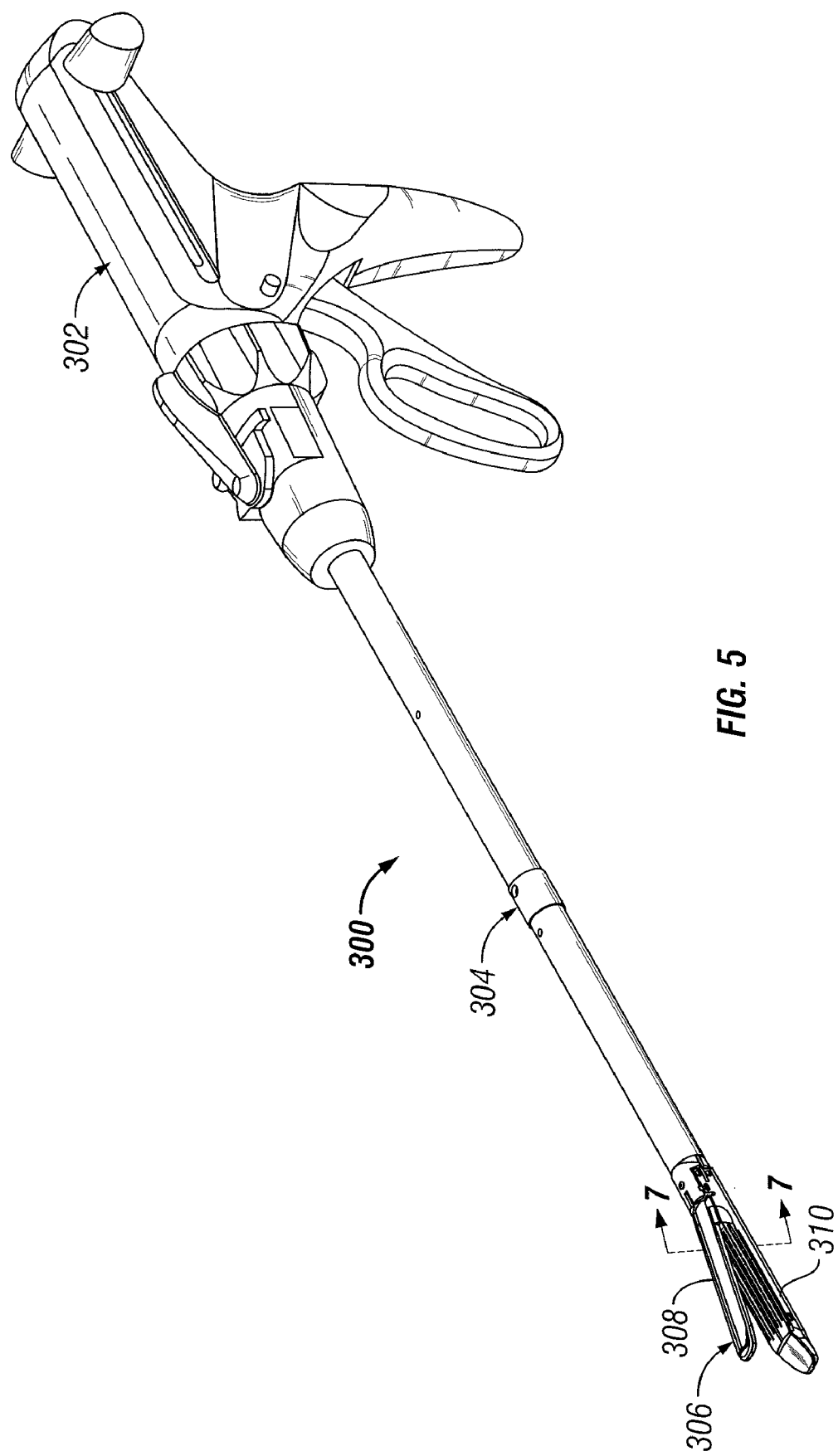
FIG. 5 is a perspective view of yet another surgical stapling instrument constructed in accordance with the present disclosure.
Figure 6:
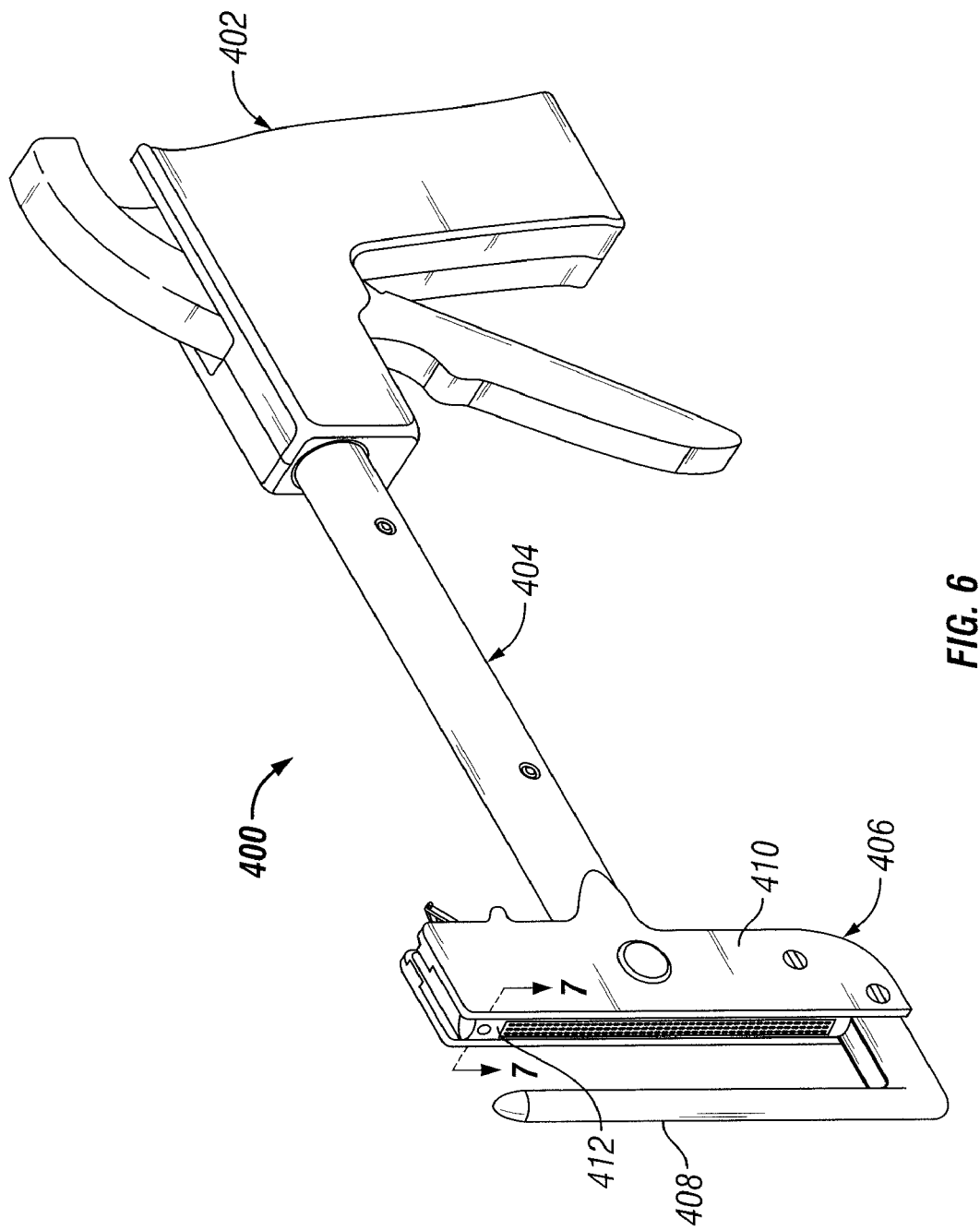
FIG. 6 is a perspective view of still another surgical stapling instrument constructed in accordance with the present disclosure.
Figure 6A:
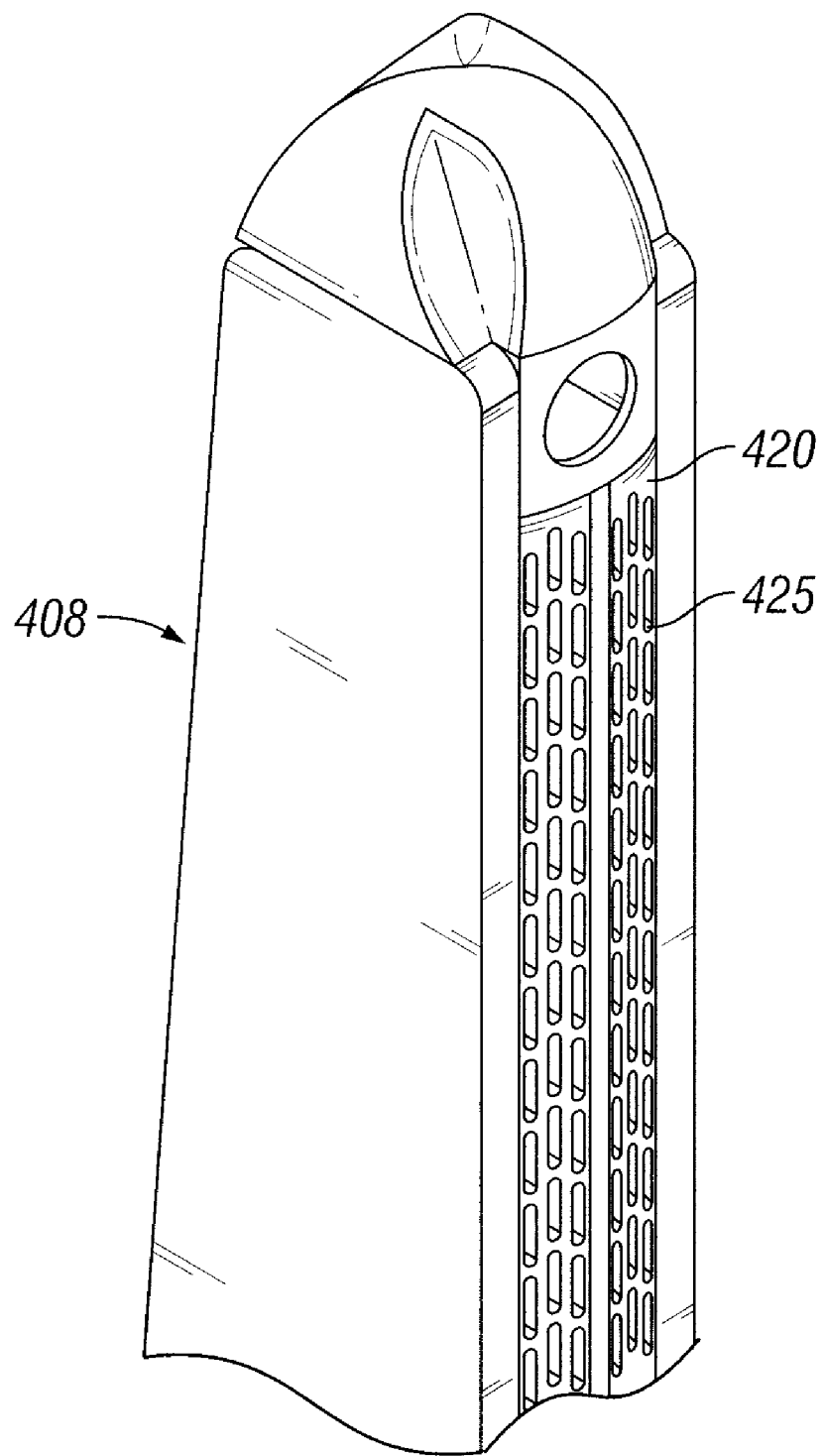
FIG. 6A is a perspective view of a portion of an anvil member of FIG. 6.

Turning now to FIGS. 5 and 7, a surgical stapling instrument, of the laparoscopic type for performing surgical anastomotic stapling, in accordance with another embodiment of the disclosure, is generally designated as 300. Surgical stapling instrument 300 includes a handle 302, an operative tool 306, and an elongated shaft 304 for interconnecting operative tool 306 to handle 302. In general, operative tool 306 is designed to clamp over and then to staple and divide tissue held therein. Accordingly, as seen in FIG. 5, operative tool 306 is a pair of opposed jaws including an anvil member 308 and a staple cartridge 310 pivotally coupled to one another.

Staple cartridge 310 of surgical stapling instrument 300 includes a stepped tissue contacting surface 121 similar to tissue contacting surface 121 of staple cartridge 204 of surgical stapling instrument 200. Accordingly, reference is made to FIG. 7 and the above detailed discussion of tissue contacting surface 121 of staple cartridge 204 for an illustration and a discussion of tissue contacting surface 121 of staple cartridge 310 of surgical stapling instrument 300.

In operation, surgical stapling instrument 300 is fired similarly to and in accordance with other known surgical stapling instruments. For a detailed discussion of the approximation and firing of surgical stapling instrument 300, reference is made to commonly assigned U.S. Pat. No. 5,865,361, currently assigned to Tyco Healthcare Group LP, the entire contents of which is incorporated herein by reference.

Following the firing of surgical stapling instrument 300 the resulting tissue interface, as seen in cross-section, is substantially similar to the resulting tissue interface, as seen in cross-section, following the firing of surgical stapling instruments 100 and 200. Accordingly, as seen in FIG. 16, surgical fasteners 125a and 125b (i.e. the two rows of surgical fasteners furthest from knife cut line "C") serve to hold tissues "A" and "B" to one another while surgical fasteners 125c (i.e. the row of surgical fasteners closest to knife cut line "C") serve to provide the hemostasis.

While surgical stapling instrument 300 is a linear-type surgical stapler as compared to surgical stapling instrument 100, it is envisioned and within the scope of the present disclosure, that surgical stapling instrument 300 can include a tissue contacting surface having a cross-sectional profile for at least one of the anvil and the staple cartridge which is substantially similar to the tissue contacting surfaces of the anvil and the staple cartridge of surgical stapling instrument 100, as shown in FIGS. 3A-3D.

Turning now to FIGS. 6, 6A, 7, and 7A, a surgical stapling instrument, of the transverse anastomosis type for performing surgical anastomotic stapling, in accordance with yet another embodiment of the disclosure, is generally designated as 400. Surgical stapling instrument 400 includes a handle 402, a barrel 404 extending from handle 402, and an arm 406 extending from the distal end of barrel 404. Surgical stapling instrument 400 further includes an anvil member 408 orthogonally affixed to a distal end of arm 406 and a staple cartridge receiver 410 operatively coupled to the distal end of barrel 404 for holding a disposable staple cartridge 412 thereon. Anvil member 408 is illustrated in further detail in FIG. 6A and includes a tissue contacting surface 420 wherein tissue contacting surface 420 has a plurality of pockets 425 that substantially align with retention slots 123 (FIG. 7). Cooperative alignment between pockets 425 and retention slots 123 form completed surgical fasteners 125 upon actuation of the actuation mechanism in surgical stapling instrument 400.

Staple cartridge 412 of surgical stapling instrument 400 includes a stepped tissue contacting surface 121 similar to tissue contacting surface 121 of staple cartridge 204 of surgical stapling instrument 200. Accordingly, reference is made to FIG. 7 and the above detailed discussion of tissue contacting surface 121 of staple cartridge 204 for an illustration and a discussion of tissue contacting surface 121 of staple cartridge 412 of surgical stapling instrument 400. Further still, staple cartridge 412 may include knife track 222 for slidably receiving a knife (not shown) therein.

Figure 7A:
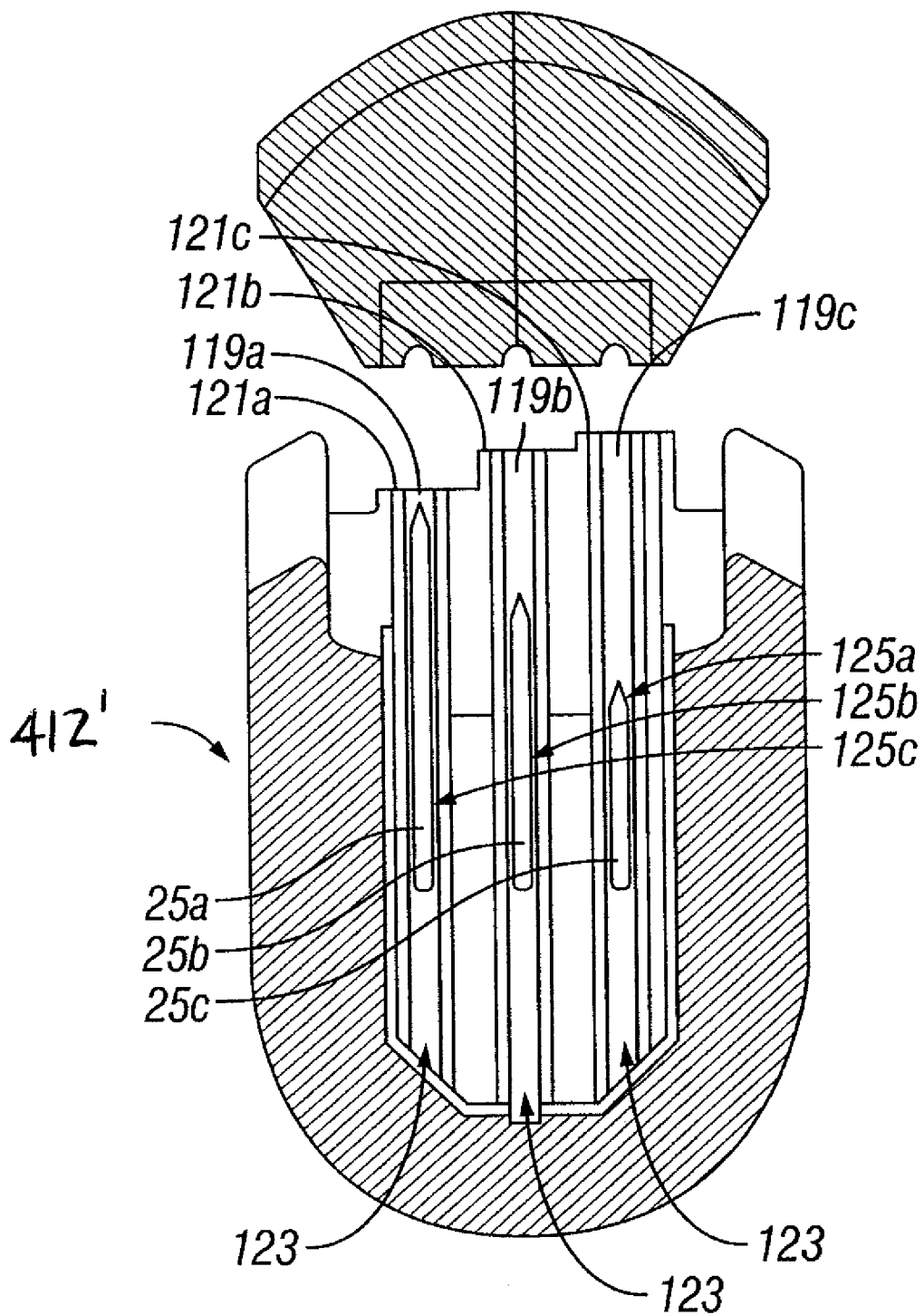
FIG. 7A is a schematic cross-sectional side elevational view of an alternate embodiment of the distal portion of the surgical stapling instrument of FIG. 6

In a further embodiment of the present disclosure, staple cartridge 412' is illustrated in FIG. 7A and discussed in detail hereinafter. Staple cartridge 412' is similar to staple cartridge 412, but only includes three rows 119a-c of retention slots 123 disposed between outer walls of staple cartridge 412'. As in the previously discussed embodiment, each row 119a-c includes a plurality of surgical fasteners wherein surgical fasteners in row 119a have a different leg length from surgical fasteners disposed in row 119b, while surgical fasteners disposed in row 119c have a leg length that is different from at least one of rows 119a or 119b. This embodiment of the staple cartridge does not include a knife track. The arrangement and interrelationship of tissue contacting surfaces 125a-c is similar to that previously disclosed with reference to FIG. 7.

In operation, surgical stapling instrument 400 is fired similarly to and in accordance with other known surgical stapling instruments. For a detailed discussion of the approximation and firing of surgical stapling instrument 400, reference is made to commonly assigned U.S. Pat. No. 5,964,394, currently assigned to Tyco Healthcare Group LP, the entire contents of which is incorporated herein by reference.

Following the firing of surgical stapling instrument 400 the resulting tissue interface, as seen in cross-section, is substantially similar to the resulting tissue interface, as seen in cross-section, following the firing of surgical stapling instruments 100-300. Accordingly, as seen in FIG. 16, surgical fasteners 125a and 125b (i.e. the two rows of surgical fasteners furthest from knife cut line "C") serve to hold tissues "A" and "B" to one another while surgical fasteners 125c (i.e. the row of surgical fasteners closest to knife cut line "C") serve to provide the hemostasis.

While surgical stapling instrument 400 is a linear-type surgical stapler as compared to surgical stapling instrument 100, it is envisioned and within the scope of the present disclosure, that surgical stapling instrument 400 can include a tissue contacting surface having a cross-sectional profile for at least one of the anvil and the staple cartridge which is substantially similar to the tissue contacting surfaces of the anvil and the staple cartridge of surgical stapling instrument 100, as shown in FIGS. 3A-3D.

While each of the surgical stapling instruments described above and shown herein are configured and adapted to fire surgical fasteners 125, it is envisioned and within the scope of the present disclosure, that tissue contacting surfaces of surgical instruments used in connection with applying two-part fasteners can also have stepped configurations as shown and described herein. A typical two-part surgical fastener applying instrument is shown and described in commonly assigned U.S. Pat. No. 5,573,169, currently assigned to Tyco Healthcare Group LP, the entire contents of which is incorporated herein by reference.

Figure 8:
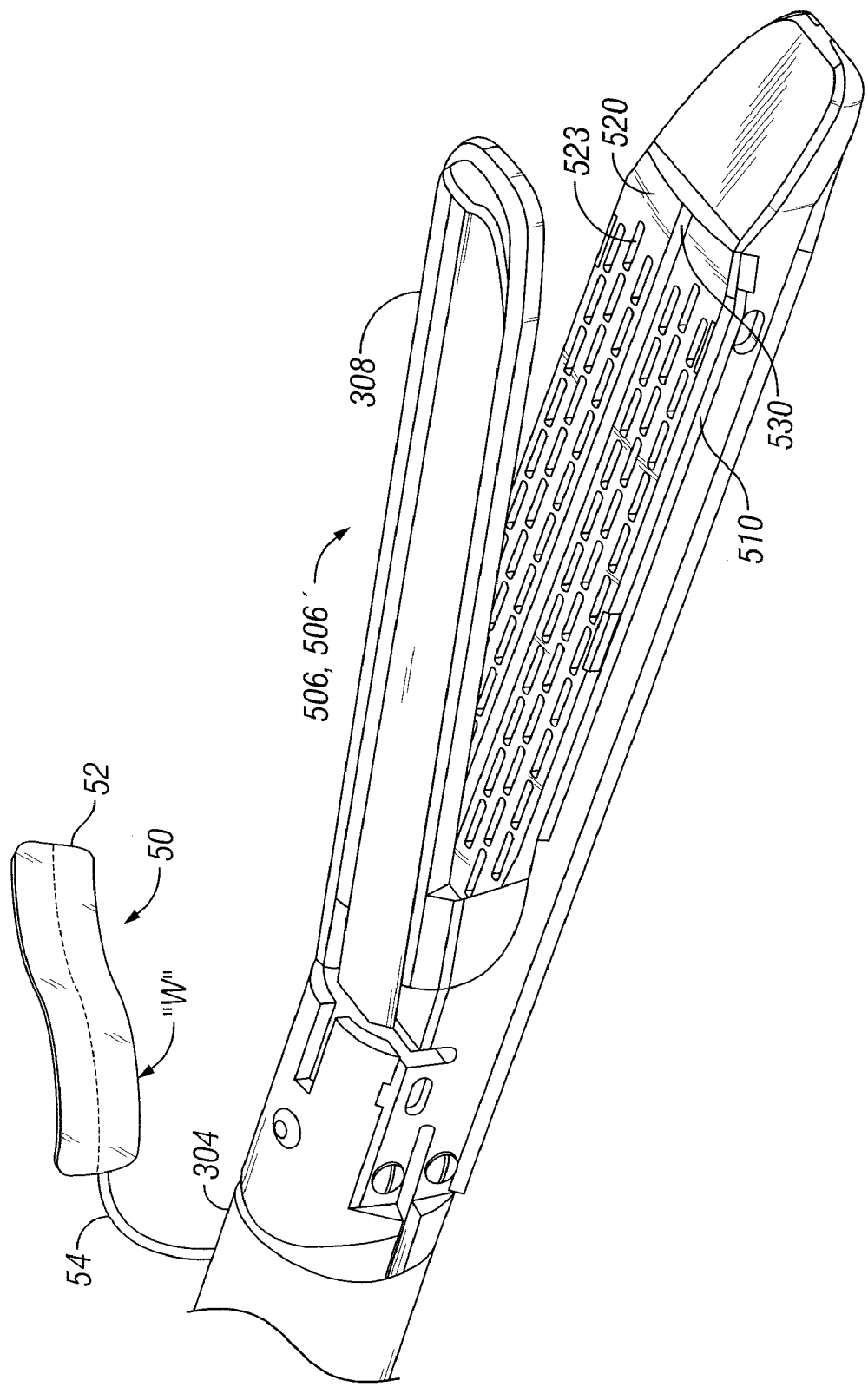
FIG. 8 is a perspective view of a staple cartridge according to another embodiment of the present disclosure.
Figure 9:
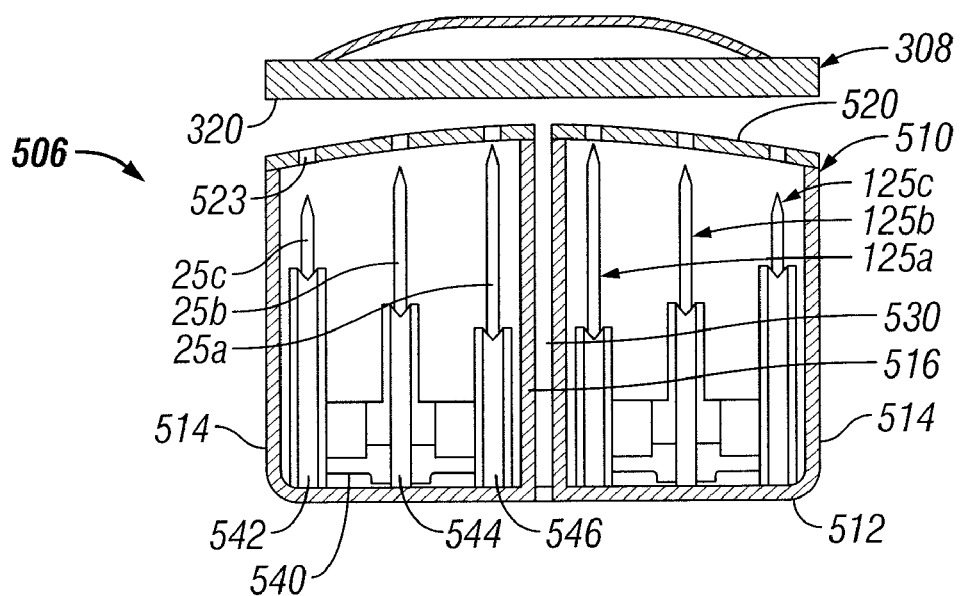
FIG. 9 is a cross-sectional end view of the staple cartridge of FIG. 8 showing a first arrangement of surgical fasteners.
Figure 10:
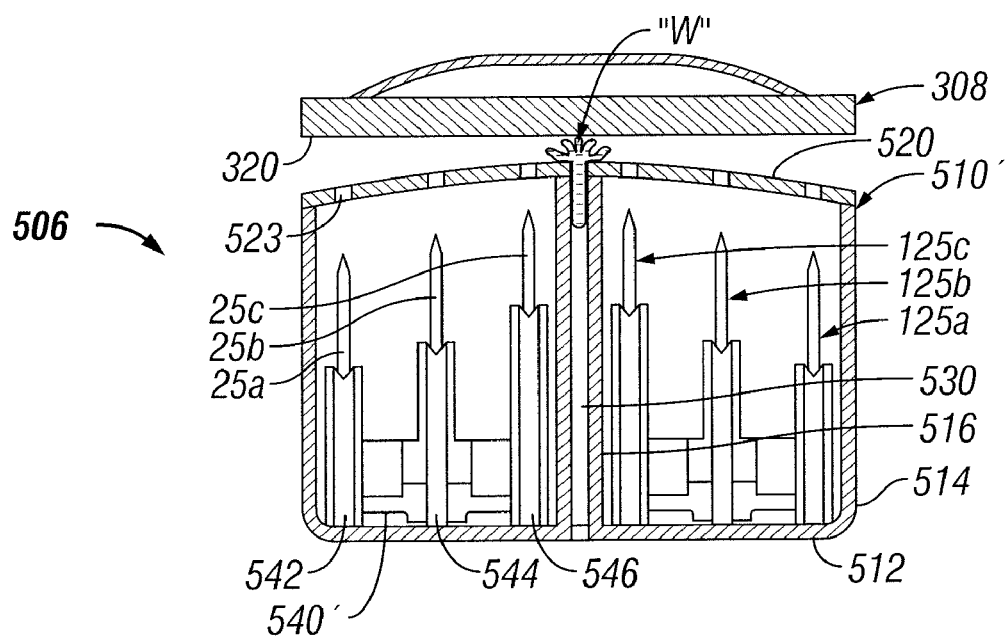
FIG. 10 is an alternate embodiment of the staple cartridge of FIG. 9 illustrating a second embodiment of the surgical fasteners.

In one further embodiment of the present disclosure, as illustrated in FIGS. 8-10, surgical stapling apparatus 300 includes an operative tool 506 disposed at one end of elongated shaft 304. Operative tool 506 includes anvil member 308 and a staple cartridge 510. Staple cartridge 510 may be included in a disposable surgical stapling apparatus or in a reusable surgical stapling apparatus. In particular, staple cartridge 510 includes a tissue contacting surface 520 having a plurality of retention slots 523 disposed therein and arranged in rows that are substantially aligned with a longitudinal axis of staple cartridge 510. As seen in FIG. 8, each row of retention slots 523 is longitudinally offset from an adjacent row of retention slots. In particular, an optional knife channel 530 is disposed along the longitudinal axis of staple cartridge 510 that is adapted for slidably receiving a knife (not shown).

Referring now to FIG. 9, operative tool 506 is shown in cross-section and illustrates the several components included in staple cartridge 510. Anvil member 308 includes a substantially planar tissue contacting surface 320 that is substantially parallel to a bottom surface 512 or parallel to a plane defined by the backspans of surgical fasteners 125a, 125b, or 125c. Staple cartridge 510 includes outer walls 514 having a first height and inner walls 516 having a second height wherein the second height is greater than the first height. Tissue contacting surface 520 is attached to inner walls 516 and to outer walls 514 and defines an angle with respect to a plane that is orthogonal to inner walls 516. Tissue contacting surface 520 defines a generally curved path between outer walls 514 (i.e. generally convex or elliptical as viewed in cross-section). Additionally, a plurality of surgical fasteners 125a-c are disposed in staple cartridge 510 wherein each row of retention pockets 523 includes a number of substantially identical surgical fasteners (i.e. 125a, 125b, or 125c). Similar to previous embodiments, legs 25a-c of surgical fasteners 125a-c have different lengths. In this embodiment, surgical fasteners 25a have a leg length of about 3.8 mm, surgical fasteners 25b have a leg length of about 3.5 mm, and surgical fasteners 25c have a leg length of about 2.5 mm. As seen in FIG. 9, surgical fasteners 125a-c are disposed in staple cartridge 510 such that surgical fasteners 125c are proximate to outer walls 514, surgical fasteners 125a are disposed proximate to inner walls 516, and surgical fasteners 125b are disposed therebetween. In cooperation with the surgical fasteners of varying height, staple cartridge 510 includes fastener ejection members 540 that include staple pushers 542, 544, and 546 of differing heights. Staple pusher 542 has the greatest height dimension, staple pusher 546 has the least height dimension, and staple pusher 544 has a height dimension therebetween. In this embodiment, surgical fasteners 125a-c are arranged to cooperate with staple pushers 546, 544, and 542 respectively. Fastener ejection member 540 is adapted for substantially vertical movement when it cooperatively engages with an actuation mechanism (not shown). An example of a suitable actuation mechanism is disclosed in U.S. Pat. No. 5,865,361 as discussed with reference to previously disclosed surgical stapling instrument 300.

Alternatively, as shown in FIG. 10, surgical fasteners 125a-c are disposed in staple cartridge 510' such that surgical fasteners 125a are proximate to outer walls 514, surgical fasteners 125c are disposed proximate to inner walls 516, and surgical fasteners 125b are disposed therebetween. Contrary to the previous embodiment, surgical fasteners 125a-c are arranged to cooperate with staple pushers 542, 544, and 546 respectively. After a number of layers of body tissue are positioned between tissue contacting surfaces 320 and 520, the actuation mechanism is actuated for sequentially ejecting surgical fasteners 125a-c through retention slots 523 whereby interaction between surgical fasteners 125a-c and anvil member 308 forms completed surgical fasteners for joining the layers of body tissue.

When tissue contacting surface 320 of anvil member 308 is repositioned proximate to tissue contacting surface 520 of staple cartridge 510', the amount of pressure applied to the layers of tissue disposed therebetween varies along a plane that is transverse to the longitudinal axis of staple cartridge 510'. Since the distance between tissue contacting surfaces 320 and 520 is at a minimum in the region nearest inner walls 516 (i.e. the centerline of staple cartridge 510'), a maximum pressure is applied to the layers of tissue disposed in this region. Conversely, the distance between tissue contacting surfaces 320 and 520 is at a maximum in the region near outer walls 514, a minimum pressure is applied to the layers disposed in this region. In addition, the proximal relationship between anvil member 308 and staple cartridge 510' defines a plurality of gaps therebetween. A first gap is defined between tissue contacting surfaces 320 and 520 (i.e. along the centerline of staple cartridge 510'), while a second gap is defined between tissue contacting surfaces 320 and 520 along outer walls 514. As seen in FIG. 10, the first gap is not equal to the second gap. Further still, a number of other gaps may be defined between tissue contacting surfaces 320 and 520 at other points of reference existing between the centerline and outer walls 514 in staple cartridge 510'. Since tissue contacting surface 520 slopes toward outer walls 514 to define a substantially uniform angle, the pressure applied to the layers of tissue disposed between tissue contacting surfaces 320 and 520 uniformly decreases from inner wall 516 to outer wall 514.

By angling tissue contacting surface 520 downwards from the centerline of staple cartridge 510', reduced compressive forces are applied to the layers of tissue disposed between tissue contacting surfaces 320 and 520 thereby minimizing trauma to the layers of tissue disposed therebetween. Therefore, layers of tissue disposed between tissue contacting surfaces 320 and 520 will have a minimum thickness nearest knife channel 530 (i.e. nearest the centerline of staple cartridge 510') and a maximum thickness nearest outer walls 514. In addition, anvil member 308 and staple cartridge 510' are dimensioned and arranged such that compressive forces applied to the layers of tissue are minimal thereby further reducing trauma to the layers of tissue. This configuration defines a gap between tissue contacting surfaces 320 and 520 that is a maximum along knife channel 530 (i.e. the centerline of staple cartridge 510 or 510') and a minimum along outer walls of staple cartridge 510 (FIG. 9) or 510' (FIG. 10).

Further still, this configuration is applicable to similar staple cartridges and anvil members as will be discussed in detail hereinafter with respect to FIGS. 11-15. When anvil member 308 is repositioned into proximity with staple cartridge 510' (i.e. in a pre-fire position) to retain layers of body tissue therebetween, the layers of tissue are compressed. The maximum compression occurs along the centerline (i.e. first or minimum gap) and urges fluid stored in the layers of tissue towards the outer edges of the tissue (i.e. away from the centerline of staple cartridge 510'). By reducing the amount of fluid retained in the layers of tissue proximal to the centerline, the overall thickness of the tissue layers decreases. The decrease in overall tissue thickness is such that a staple having a shorter leg length (i.e. surgical fastener 125c) is capable of fastening both layers of tissue while minimizing trauma to the fastened layers of tissue. The gap increases towards the outer walls of staple cartridge 510' (i.e. the amount of compression decreases) and surgical fasteners having a longer leg length (i.e. surgical fasteners 125a and 125b) are capable of fastening both layers of tissue.

Leg lengths of surgical fasteners 125c, 125b, and 125a increase in a direction moving from inner walls 516 towards outer walls 514. By providing surgical fasteners having increasing leg lengths along a plane that is orthogonal to inner walls 516, the completed (i.e. formed) surgical fasteners join increasing thicknesses of tissue without unduly traumatizing the joined layers of tissue.

Figure 11:
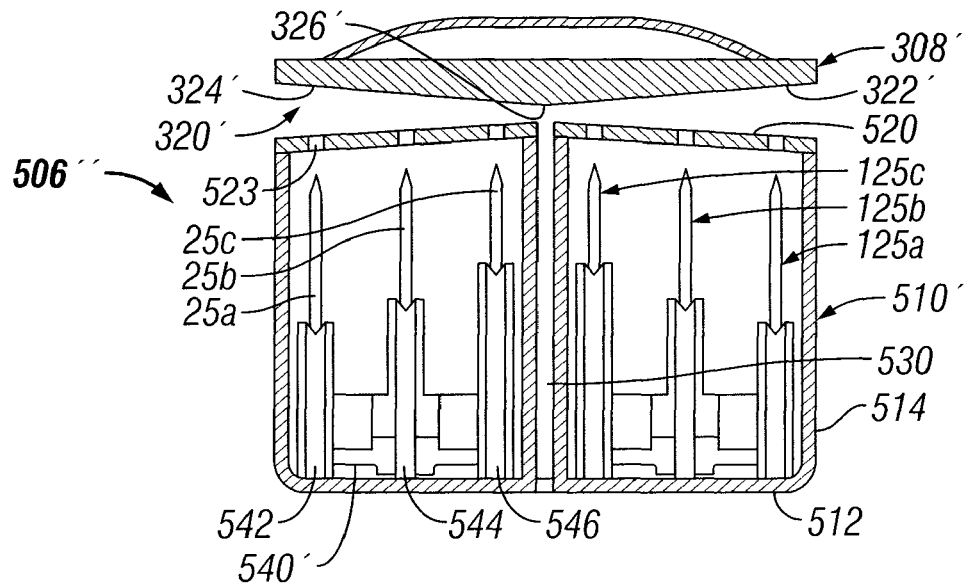
FIG. 11 is an alternate embodiment of an anvil member and the staple cartridge of FIG. 10.

In a further embodiment, as illustrated in FIG. 11, operative tool 506" includes staple cartridge 510' and anvil member 308'. Staple cartridge 510' was previously discussed in detail hereinabove with reference to FIG. 10. Tissue contacting surface 520 may define a more uniform angle (FIG. 11) than in the embodiments of FIGS. 9 and 10 wherein the angle or pitch of tissue contacting surface is substantially constant between inner walls 516 and outer walls 514. Anvil member 308' includes tissue contacting surface 320' having tapered surfaces 322' and 324'. Surfaces 322' and 324' are connected to outer walls of anvil member 308' while extending inwards (i.e. towards the centerline of staple cartridge 510') and downwards (i.e. towards tissue contacting surface 520) thereby defining an angle. It is envisioned that the angle defined by tapered surfaces 322' and 324' will be substantially similar to the angle defined by tissue contacting surface 520, but in an opposed direction forming a generally V-shaped configuration. Thus, compressive forces applied to the layers of tissue will be further reduced thereby further reducing the trauma to layers of tissue disposed between tissue contacting surfaces 520 and 320'. As in the embodiment of FIG. 10, the maximum pressure applied to the layers of tissue will exist in the region near knife channel 530 while pressures applied to the layers of tissue will decrease uniformly towards outer walls 514. Formation and location of surgical fasteners 125a-c is substantially similar to that of the embodiment of FIG. 10 along with the attendant advantages.

Figure 12:
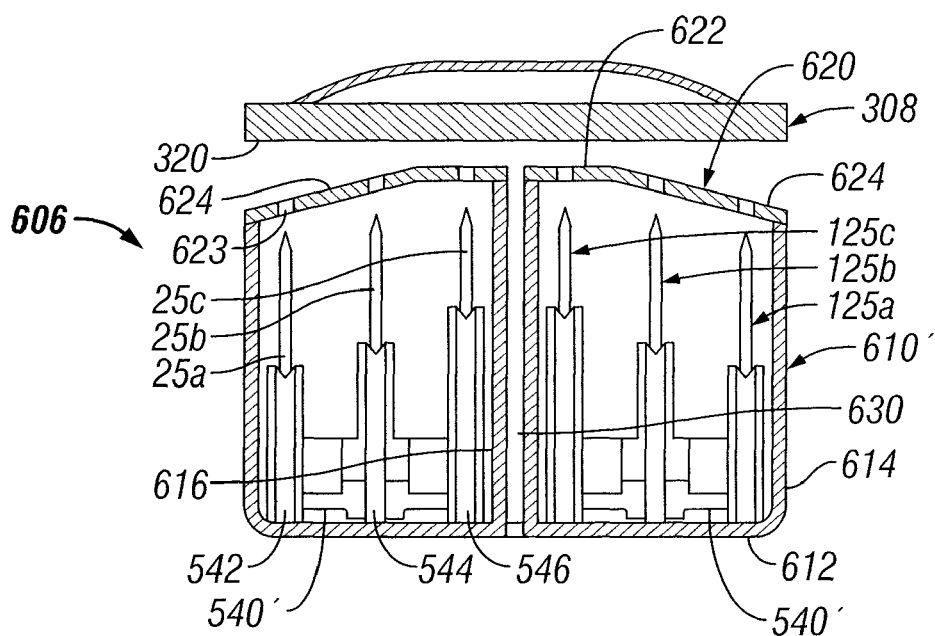
FIG. 12 is a further embodiment of the staple cartridge of FIG. 8.

Referring now to FIG. 12, a further embodiment of the present disclosure is shown as part of operative tool 606. Operative tool 606 includes a staple cartridge 610 and anvil member 308. In this embodiment, tissue contacting surface 620 includes surfaces 622 and 624. Surface 622 is bisected along its longitudinal axis by knife channel 630 and substantially parallel to a bottom surface 612 or parallel to a plane defined by the backspans of surgical fasteners 125a, 125b, or 125c. In addition, surface 622 has a width dimension sufficient to accommodate at least one row of retention slots 623 on each side of knife channel 630. Surface 624 connects outer edges of surface 622 to outer walls 614 defining an angle on either side of knife channel 630 with respect to a plane that is substantially orthogonal to inner walls 616 (i.e. substantially parallel to surface 622) and has a width dimension sufficient to accommodate at least one row of retention slots on each side of knife channel 630. Staple cartridge 610 includes a plurality of surgical fasteners 125a-c and fastener ejection members 540 that were previously discussed in detail with respect to FIGS. 9 and 10. In particular, staple cartridge 610 includes the arrangement of surgical fasteners 125a-c and fastener ejection members 540 as described with respect to staple cartridge 510' (FIGS. 10 and 11).

Similarly to operative tool 506, tissue contacting surface 320 is repositioned proximate to tissue contacting surface 620 of staple cartridge 610. In this arrangement, the amount of pressure applied to the layers of tissue disposed therebetween varies along a plane that is transverse to the longitudinal axis of staple cartridge 610. Specifically, the distance between tissue contacting surface 320 and surface 622 is a minimum, a maximum pressure is applied to the layers of tissue disposed in this region. Conversely, the distance between tissue contacting surface 320 and surfaces 624 is at a maximum in the region near outer walls 614, a minimum pressure is applied to the layers disposed in this region. Since surface 624 slopes toward outer walls 614 to define a substantially uniform angle, the pressure applied to the layers of tissue disposed between tissue contacting surface 320 and surfaces 624 uniformly decreases from an outer edge of surface 622 towards outer wall 614.

By angling surface 624 downwards from the edge of surface 622, reduced compressive forces are applied to the layers of tissue disposed between tissue contacting surface 320 and surfaces 624 thereby minimizing trauma to the layers of tissue disposed therebetween. Layers of tissue disposed between tissue contacting surfaces 320 and 620 will have a minimum thickness nearest knife channel 630 and a maximum thickness nearest outer walls 614. In addition, anvil member 308 and staple cartridge 610 are dimensioned and arranged such that compressive forces applied to the layers of tissue are minimal thereby further reducing trauma to the layers of tissue.

Leg lengths of surgical fasteners 125c, 125b, and 125a increase in a direction moving from inner walls 616 towards outer walls 614. By providing surgical fasteners having increasing leg lengths along a plane that is orthogonal to inner walls 616, the completed (i.e. formed) surgical fasteners join increasing thicknesses of tissue without unduly traumatizing the joined layers of tissue.

Figure 13:
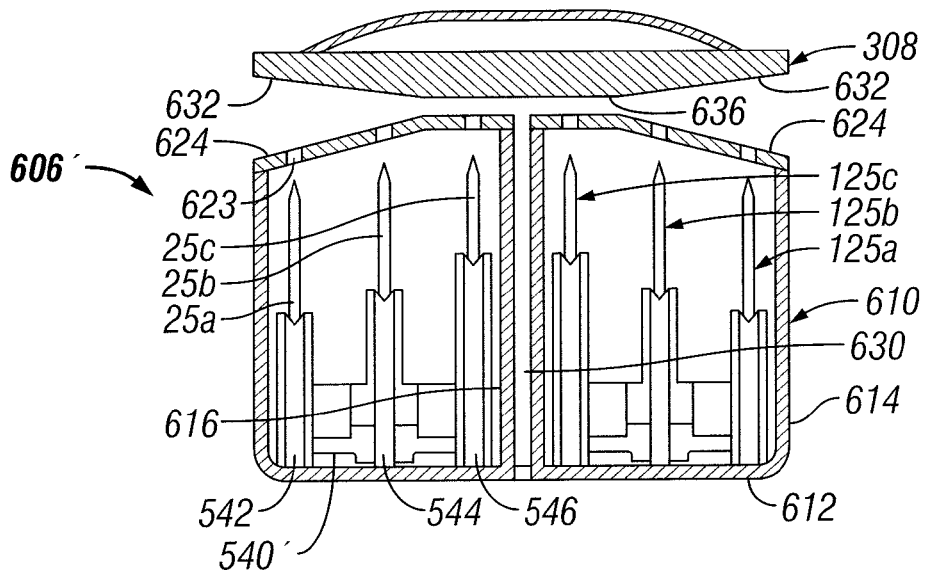
FIG. 13 is another embodiment of the anvil member and the staple cartridge of FIG. 12.

In a further embodiment, operative tool 606' is illustrated in FIG. 13. Operative tool 606' includes staple cartridge 610, that was described in detail hereinabove with respect to FIG. 12, and anvil member 608. Anvil member 608 includes a tissue contacting surface 620 formed from surfaces 632 and 636. Surface 636 is substantially parallel to surface 622 and has a width dimension that is substantially similar to the width dimension of surface 622. Surfaces 632 are tapered and connected to outer walls of anvil member 608 and extend inwards (i.e. towards the centerline of staple cartridge 610) and downwards (i.e. towards tissue contacting surface 620) thereby defining an angle. It is envisioned that the angle defined by tapered surfaces 632 will be substantially similar to the angle defined by surfaces 624, but in an opposed direction. Thus, compressive forces applied to the layers of tissue will be further reduced thereby further reducing the trauma to layers of tissue disposed between surfaces 624 and 632. As in the embodiment of FIG. 10, the maximum pressure applied to the layers of tissue will exist in the region along surface 622 while pressures applied to the layers of tissue will decrease uniformly along surfaces 624 towards outer walls 614. Formation and location of surgical fasteners 125a-c is substantially similar to that of the embodiment of FIG. 12 along with the attendant advantages.

Figure 14:
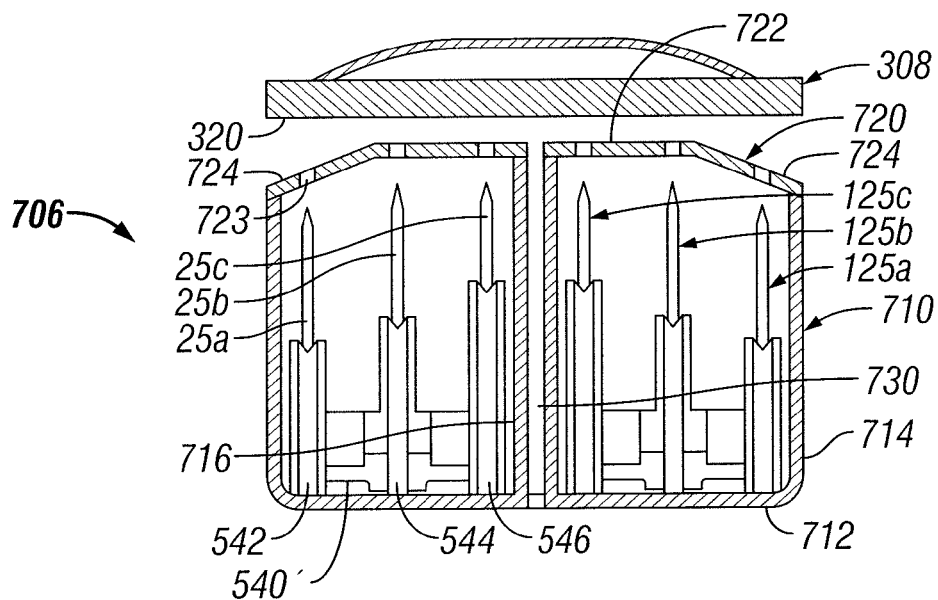
FIG. 14 is another embodiment of the staple cartridge and anvil member of FIG. 8.

In yet another embodiment, operative tool 706 is illustrated in FIG. 14. Staple cartridge 710 is similar to staple cartridge 610. The differences between staple cartridges 610 and 710 will be discussed hereinafter. As in staple cartridge 610 (FIG. 12), staple cartridge 710 includes tissue contacting surface 720 formed from surfaces 722 and 724. Surface 722 differs from surface 622 in that it has a width dimension sufficient to accommodate at least two rows of surgical fasteners. As in staple cartridge 610, surfaces 724 are attached to outer edges of surface 722 and outer walls 714 to define angles. The interaction between staple cartridge 710 and anvil member 308 for capturing tissue and forming surgical fasteners is substantially similar to the interaction between staple cartridge 610 and anvil member 308 and, for the sake of brevity, will not be repeated herein.

Figure 15:
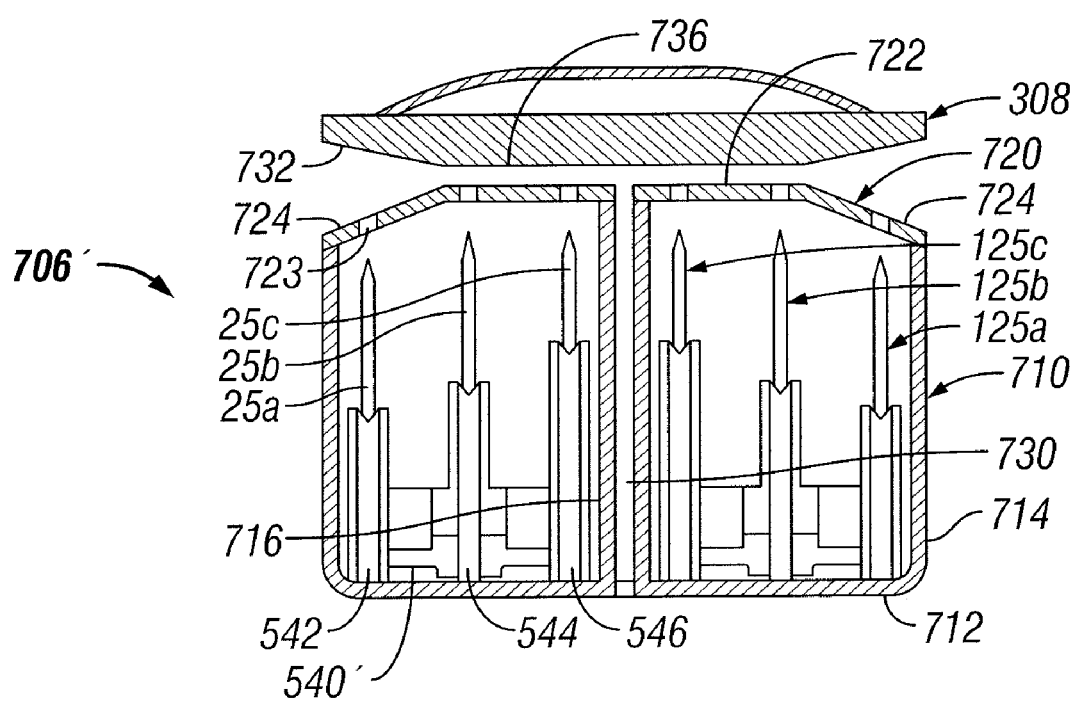
FIG. 15 is alternate embodiment of an anvil member with the staple cartridge of FIG. 14.

In a further embodiment, operative tool 706' is shown in FIG. 15 and includes staple cartridge 710, as described with respect to FIG. 14, and anvil member 708. Anvil member 708 includes a tissue contacting surface 720 formed from surfaces 732 and 736. Surface 736 is substantially parallel to surface 722 and has a width dimension that is substantially similar to the width dimension of surface 722. Surfaces 732 are tapered and connected to outer walls of anvil member 708 and extend inwards (i.e. towards the centerline of staple cartridge 710) and downwards (i.e. towards tissue contacting surface 720) thereby defining an angle. It is envisioned that the angle defined by tapered surfaces 732 will be substantially similar to the angle defined by surfaces 724, but in an opposed direction. Thus, compressive forces applied to the layers of tissue will be further reduced thereby further reducing the trauma to layers of tissue disposed between surfaces 724 and 732. As in the embodiment of FIG. 14, the maximum pressure applied to the layers of tissue will exist in the region along surface 722 while pressures applied to the layers of tissue will decrease uniformly along surfaces 724 towards outer walls 714. Formation and location of surgical fasteners 125a-c is substantially similar to that of the embodiment of FIG. 14 along with the attendant advantages.

In FIG. 15, an alternate embodiment of operative tool 706' is illustrated. Operative tool 706' includes staple cartridge 710, as discussed in detail hereinabove, and anvil member 708. Anvil member 708 includes a tissue contacting surface 720 formed from surfaces 732 and 736. Surface 736 is substantially parallel to surface 722 and has a width dimension that is substantially similar to a width dimension of surface 722. Surfaces 732 are tapered and connected to outer walls of anvil member 708 and extend inwards (i.e. towards centerline of staple cartridge 710) and downwards (i.e. towards tissue contacting surface 720) thereby defining an angle. It is envisioned that the angle defined by tapered surfaces 732 will be substantially similar to the angle defined by surfaces 724, but in an opposed direction. Thus, compressive forces applied to the layers of tissue will be further reduced, thereby further reducing the trauma to the layers of tissue disposed between surfaces 724 and 732. As in the embodiment of FIG. 14, the maximum pressure applied to the layers of tissue will exist in the region along surface 722 while pressures applied to the layers of tissue will decrease uniformly along surfaces 724 towards outer walls 714. Formation and location of surgical fasteners 125a-c is substantially similar to that of the embodiment of FIG. 14 along with the attendant advantages.

Turning now to FIG. 16, a cross-section of the resulting tissue interface, following the firing of staple cartridge 510', is shown. As seen in FIG. 16, the tissue interface has a substantially tapered profile. In particular, surgical fasteners 125a and 125b (i.e. the two rows of surgical fasteners furthest from knife cut line "C") serve to hold tissues "A" and "B" to one another while surgical fasteners 125c (i.e. the row of surgical fasteners closest to knife cut line "C") serve to provide the hemostasis. This resulting cross-section is also applicable to the firing of staple cartridges 610 and 710. When staple cartridge 510 is fired, surgical fasteners 125b and 125c (i.e. the two rows of surgical fasteners furthest from knife cut line "C") serve to hold tissues "A" and "B" to one another while surgical fasteners 125a (i.e. the row of surgical fasteners closest to knife cut line "C") serve to provide the hemostasis.

In a further embodiment of the present disclosure, as shown in FIGS. 8 and 10, operative tool 506' includes a wound closure assembly 50. Wound closure assembly 50 includes at least one storage device or reservoir 52 and at least one supply line 54. Supply line 54 fluidly couples reservoir 52 to staple cartridge 510' for delivering an amount of a wound closure material "W". In particular, supply line 54 delivers wound closure material "W" into knife channel 530 such that when surgical fasteners 125a-c are formed, wound closure material "W" migrates along the layers of tissue adjacent to tissue contacting surface 520 (i.e. the target site). By providing wound closure material "W" in combination with surgical fasteners 125a-c, the bond formed between the layers of tissue has improved strength.

Compression of reservoir 52 causes wound closure material "W" contained therein to be urged through supply line 54 and dispensed via knife channel 530. Preferably, wound closure material "W" is dispensed during the staple firing procedure so that wound closure material "W" is dispensed along the length of the staple line and/or a knife cut line. Although wound closure assembly is discussed and illustrated with respect to FIG. 10, it is contemplated that wound closure assembly 50 is adaptable for use with other disclosed embodiments of staple cartridge 510' (i.e. 510, 610, or 710). It is further contemplated that an additional reservoir may be included for wound closure materials formed by combining two substances or that reservoir 52 may include a plurality of internal chambers (shown in phantom) for storing quantities of substances to be combined to form wound closure material "W". Further still, wound closure assembly 50 may be included in surgical stapling apparatus 100 (FIG. 1) wherein at least one opening 56 is disposed in a wall of anvil shaft 110 for dispensing wound closure material "W".

It is envisioned that wound closure material "W" can include one or a combination of adhesives, hemostats, sealants. Surgical biocompatible wound closure materials which can be employed in or applied the surgical instruments, especially surgical staplers, include adhesives whose function is to attach or hold organs, tissues or structures, sealants to prevent fluid leakage, and hemostats to halt or prevent bleeding. Examples of adhesives which can be employed include protein derived, aldehyde-based adhesive materials, for example, the commercially available albumin/glutaraldehyde materials sold under the trade designation BioGlue™ by Cryolife, Inc., and cyanoacrylate-based materials sold under the trade designations Indermil™ and Derma Bond™ by Tyco Healthcare Group, LP and Ethicon Endosurgery, Inc., respectively. Examples of sealants, which can be employed, include fibrin sealants and collagen-based and synthetic polymer-based tissue sealants. Examples of commercially available sealants are synthetic polyethylene glycol-based, hydrogel materials sold under the trade designation CoSeal™ by Cohesion Technologies and Baxter International, Inc. Examples of hemostat materials, which can be employed, include fibrin-based, collagen-based, oxidized regenerated cellulose-based and gelatin-based topical hemostats. Examples of commercially available hemostat materials are fibrinogen-thrombin combination materials under sold the trade designations CoStasis™ by Tyco Healthcare Group, LP, and Tisseel™ sold by Baxter International, Inc. Hemostats herein include astringents, e.g., aluminum sulfate, and coagulants.

It is to be understood that the dispensing of wound closure material "W" can be as a fluid spray of any suitable volume, including a mist, applied temporarily, continuously, or continually. Particulate material, e.g. a fine powder is contemplated to be a fluid within the scope of this disclosure.

It is provided that a number of different wound closure materials "W" can be dispensed by wound closure assembly 50 or a combination of the number of different wound closure materials "W". The wound closure material dispensed by wound closure assembly 50 can, for example, be an astringent, such as a sulfate of aluminum, which causes small blood vessels to close and helps the blood to coagulate. It is provided that wound closure material "W" can be an astringent provided in the material commercially available under the trade designation No Nix Styptic Pencils from Requa™, Inc.

In addition, while each of the surgical stapling instruments described above and shown herein include tissue contacting surfaces having a stepped profile, it is envisioned that any of the surgical stapling instruments disclosed herein can have tissue contacting surfaces having any one of a number of profiles including and not limited to angles, conical, tapered, arcuate and the like, as disclosed in commonly assigned U.S. patent application Ser. No. 10/411,686, filed on May 11, 2003, entitled "Surgical Stapling Apparatus Including an Anvil and Cartridge Each Having Cooperating Mating Surfaces," currently assigned to Tyco Healthcare Group LP, the entire contents of which is incorporated herein by reference.

It will be understood that various modifications may be made to the embodiments of the presently disclosed surgical stapling instruments. Therefore, the above description should not be construed as limiting, but merely as exemplifications of embodiments. Those skilled in the art will envision other modifications within the scope and spirit of the present disclosure.

What is claimed is:

1. A surgical stapling instrument comprising:
   an anvil having a first annular array of staple forming depressions and a second annular array of staple forming depressions;
   a staple retaining portion having a first tissue contacting surface with a first height and a second tissue contacting surface with a second height, the second height being different from the first height, the first tissue contacting surface defining a first plane and the second tissue contacting surface defining a second plane that is parallel to the first plane;
   a first annular array of staple retaining slots disposed in the first tissue contacting surface of the staple retaining portion and arranged for alignment with the first annular array of staple forming depressions;
   a second annular array of staple retaining slots disposed in the second tissue contacting surface of the staple retaining portion and arranged for alignment with the second annular array of staple forming depressions;
   a first plurality of staples disposed in the first annular array of staple retaining slots, each staple in the first plurality of staples having a first leg length, the first plurality of staples movable through the first annular array of staple retaining slots towards the first annular array of staple forming depressions of the anvil; and
   a second plurality of staples disposed in the second annular array of staple retaining slots, each staple in the second plurality of staples having a second leg length that is different from the first leg length, the second plurality of staples movable through the second annular array of staple retaining slots towards the second annular array of staple forming depressions of the anvil.

2. The surgical stapling instrument of claim 1, wherein a tissue compression gradient is defined such that tissue located between the first annular array of staple forming depressions and the first annular array of staple retaining slots is subjected to a first pressure and tissue located between the second annular array of staple forming depressions and the second annular array of staple retaining slots is subjected to a second pressure that is different from the first pressure.

3. The surgical stapling instrument of claim 1, wherein the first plane is vertically spaced from the second plane.

4. The surgical instrument of claim 1, wherein the anvil includes a first surface defining a first plane and a second surface defining a second plane, the first and second planes being vertically spaced.

5. The surgical instrument of claim 1, wherein the first plane is spaced apart from the second plane.

6. The surgical instrument of claim 1, wherein the first leg length is longer than the second leg length.

7. The surgical instrument of claim 1, further comprising a knife blade disposed adjacent the first annular array of staple retaining slots.

8. A surgical stapling instrument comprising:
   an anvil having a first annular array of staple forming depressions and a second annular array of staple forming depressions, the anvil including a first surface defining a first plane and a second surface defining a second plane, the first and second planes being vertically spaced;
   a staple retaining portion having a first tissue contacting surface with a first height and a second tissue contacting surface with a second height, the second height being different from the first height, the first tissue contacting surface defining a first plane and the second tissue contacting surface defining a second plane that is parallel to the first plane;
   a first annular array of staple retaining slots disposed in the staple retaining portion and arranged for alignment with the first annular array of staple forming depressions;
   a second annular array of staple retaining slots disposed in the staple retaining portion and arranged for alignment with the second annular array of staple forming depressions;
   a first plurality of staples disposed in the first annular array of staple retaining slots, each staple in the first plurality of staples having a first leg length; and
   a second plurality of staples disposed in the second annular array of staple retaining slots, each staple in the second plurality of staples having a second leg length that is different from the first leg length.

9. The surgical stapling instrument of claim 8, wherein a tissue compression gradient is defined such that tissue located between the first annular array of staple forming depressions and the first annular array of staple retaining slots is subjected to a first pressure and tissue located between the second annular array of staple forming depressions and the second annular array of staple retaining slots is subjected to a second pressure that is different from the first pressure.

10. The surgical stapling instrument of claim 8, wherein the first plane is vertically spaced from the second plane.

11. The surgical stapling instrument of claim 10, wherein the first annular array of staple retaining slots is defined in the first tissue contacting surface and the second annular array of staple retaining slots is defined in the second tissue contacting surface.

12. The surgical instrument of claim 8, wherein the first plane is spaced apart from the second plane.

13. The surgical instrument of claim 8, wherein the first leg length is longer than the second leg length.

14. The surgical instrument of claim 8, further comprising a knife blade disposed adjacent the first annular array of staple retaining slots.

* * * * *